United States Patent
Guedat et al.

(10) Patent No.: US 9,682,943 B2
(45) Date of Patent: Jun. 20, 2017

(54) BENZYLIDENEGUANIDINE DERIVATIVES AND THERAPEUTIC USE FOR THE TREATMENT OF PROTEIN MISFOLDING DISEASES

(71) Applicants: Medical Research Council, Swindon (GB); InFlectis BioScience, Nantes (FR)

(72) Inventors: Philippe Guedat, Montenois (FR); Anne Bertolotti, Cambridge (GB)

(73) Assignees: MEDICAL RESEARCH COUNCIL, Swindon (GB); INFLECTIS BIOSCIENCE, Nantes (FR)

(*) Notice: Subject to any disclaimer, the term of this patent is extended or adjusted under 35 U.S.C. 154(b) by 0 days.

(21) Appl. No.: 14/760,350

(22) PCT Filed: Jan. 10, 2014

(86) PCT No.: PCT/EP2014/050422
§ 371 (c)(1),
(2) Date: Jul. 10, 2015

(87) PCT Pub. No.: WO2014/108520
PCT Pub. Date: Jul. 17, 2014

(65) Prior Publication Data
US 2016/0046589 A1    Feb. 18, 2016

(30) Foreign Application Priority Data
Jan. 10, 2013  (GB) .................................. 1300435.3

(51) Int. Cl.
| | | |
|---|---|---|
| C07D 213/61 | (2006.01) |
| C07C 281/18 | (2006.01) |
| A61K 31/155 | (2006.01) |
| A61K 31/44 | (2006.01) |
| C07D 253/075 | (2006.01) |
| A61K 31/53 | (2006.01) |
| A61K 45/06 | (2006.01) |
| A61K 31/165 | (2006.01) |
| A61K 31/216 | (2006.01) |
| C07C 281/16 | (2006.01) |

(52) U.S. Cl.
CPC ........ *C07D 253/075* (2013.01); *A61K 31/155* (2013.01); *A61K 31/165* (2013.01); *A61K 31/216* (2013.01); *A61K 31/44* (2013.01); *A61K 31/53* (2013.01); *A61K 45/06* (2013.01); *C07C 281/16* (2013.01); *C07C 281/18* (2013.01); *C07D 213/61* (2013.01)

(58) Field of Classification Search
None
See application file for complete search history.

(56) References Cited

U.S. PATENT DOCUMENTS 3,541,218 A    11/1970  Marshall et al.

FOREIGN PATENT DOCUMENTS

| CA | 958018 | 11/1974 |
| WO | WO93/03714 | 3/1993 |
| WO | WO 02/11715 | 2/2002 |

(Continued)

OTHER PUBLICATIONS

Hughes, BMJ, vol. 324, Feb. 2002, pp. 466-469.*

(Continued)

*Primary Examiner* — Zinna Northington Davis
(74) *Attorney, Agent, or Firm* — McDonnell Boehnen Hulbert & Berghoff LLP

(57) ABSTRACT

The present invention relates to a compound of formula (I), or a tautomer and/or a pharmaceutically acceptable salt thereof, wherein: $R_1$ is alkyl, Cl, F or Br; $R_2$ is H or F; $R_3$ is selected from H and alkyl; $R_4$ is selected from H and $C(O)R_6$; $R_5$ is H; or $R_4$ and $R_5$ are linked to form a heterocyclic group which is optionally substituted with one or more $R_{10}$ groups; $R_6$ is selected from $R_7$, $OR_7$ and $NR_8R_9$; $R_7$, $R_8$ and $R_9$ are each independently selected from alkyl, cycloalkyl, aralkyl, cycloalkenyl, heterocyclyl and aryl, each of which is optionally substituted with one or more $R_{10}$ groups; each $R_{10}$ is independently selected from halogen, OH, CN, $NO_2$, COO-alkyl, aralkyl, $SO_2$-alkyl, $SO_2$-aryl, COOH, CO-alkyl, CO-aryl, $NH_2$, NH-alkyl, N(alkyl)$_2$, $CF_3$, alkyl and alkoxy; X and Z are each independently $CR_{11}$, and Y is selected from $CR_{11}$ and N; and $R_{11}$ is H or F; for use in treating a disorder associated with protein misfolding stress and in particular associated with accumulation of misfolded proteins.

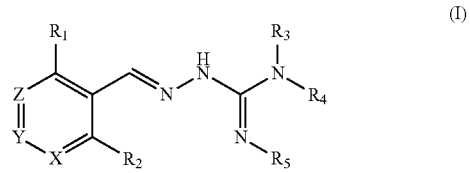

(I)

13 Claims, 6 Drawing Sheets

(56) References Cited

FOREIGN PATENT DOCUMENTS

WO    WO 2005/031000 A2  *  4/2005

OTHER PUBLICATIONS

Jiang et al, "Synthesis and biological evaluation of novel 2-(2-arylmethylene)hydrazinyl-4-aminoquina zoline derivatives as potent antitumor agents," European Journal of medicinal Chemistry, vol. 54, Aug. 1, 2012, pp. 534-541.
Tribouillard-Tanvier, et al, "Antihypertensive drug guanabenz is active in vio against both yeast and mammalian prions," PLOS One, Public Library of Science, vol. 3., No. 4, Jan. 1, 2008, p. 2.
Tsaytler et al, "Selective Inhibition of a Regulatory subunit of Protein Phosphatase 1 Restores Proteostasis," Science, vol. 332, No. 6025, Apr. 1, 2011, pp. 91-94.
International Search Report and Written Opinion mailed May 13, 2014 for International Application No. PCT/EP2014/050422 filed Jan. 10, 2014.

* cited by examiner

BENZYLIDENEGUANIDINE DERIVATIVES AND THERAPEUTIC USE FOR THE TREATMENT OF PROTEIN MISFOLDING DISEASES

This application is a U.S. national phase application of International Patent Application No. PCT/EP2014/050422 filed on Jan. 10, 2014, which claims the benefit of Great Britain patent application no. 1300435.3, filed Jan. 10, 2013.

The present invention relates to compounds that have potential therapeutic applications in treating disorders associated with protein misfolding stress and in particular with an accumulation of misfolded proteins. In particular, the invention provides compounds that are capable of exhibiting a protective effect against cytotoxic endoplasmic reticulum (ER) stress.

BACKGROUND TO THE INVENTION

The compound 2-(2,6-dichlorobenzylidene)hydrazinecarboximidamide, also referred to as guanabenz, is an alpha agonist of the alpha-2 type that is used as an antihypertensive drug.

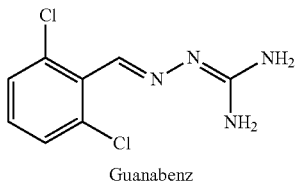 [SMILES: NC(N)=N/N=C/c1c(Cl)cccc1Cl]

Guanabenz

Various derivatives of guanabenz have also been reported. For example, U.S. Pat. No. 3,982,020 (Sandoz, Inc.) discloses substituted benzylidene hydrazines and their use as hypoglycemic-antihyperglycemic agents, anti-obesity agents and anti-inflammatory agents. US 2004/0068017 (Bausch & Lomb Inc.) discloses substituted benzylidene hydrazines that are capable of increasing the activity of gelatinase A in ocular cells. The molecules have applications in the treatment of primary open angle glaucoma. WO 2008/061647 (Acure Pharma AB) discloses the use of N-(2-chloro-3,4,-dimethoxybenzylideneamino)guanidine as a VEGFR inhibitor and its associated applications in the treatment or prevention of undesired blood vessel formation during tumour growth and/or inflammatory conditions. WO 2005/031000 (Acadia Pharmaceuticals, Inc.) discloses substituted benzylidene hydrazines and their use in treating acute pain and chronic neuropathic pain. Finally, EP 1908464 (CNRS) discloses guanabenz and chloroguanabenz and their use in the treatment of polyglutamine expansion associated diseases, including Huntington's disease.

More recently it has been reported that guanabenz has therapeutic potential in a number of other areas. Guanabenz, was recently noted to have anti-prion activity (D. Tribouillard-Tanvier et al., 2008 PLoS One 3, e1981). It has been reported that its activity in protecting against protein misfolding is surprisingly much broader and includes attenuating accumulation of mutant Huntingtin in cell-based assays (WO 2008/041133) and protection against the lethal effects of expression of misfolding prone Insulin Akita mutant in the endoplasmic reticulum (ER) of Min6 and INS-1 pancreatic beta-cells (P. Tsaytler, H. P. Harding, D. Ron and A. Bertolotti, Science, 332, 1 Apr. 2011, 91-94).

Guanabenz has also been shown to promote survival of HeLa cells exposed to otherwise cytotoxic ER-stress induced by the N-glycosylation inhibitor tunicamycin, in a dose-dependent manner (P. Tsaytler, H. P. Harding, D. Ron and A. Bertolotti, Science, 332, 1 Apr. 2011, 91-94). Quantitative assessment of cell viability revealed that guanabenz doubled the number of cells surviving ER stress with a median effective concentration of ~0.4 μM. Neither the α2-adrenergic receptor agonist clonidine, nor the α2-adrenergic receptor antagonist efaroxan protected cells from cytotoxic ER stress and efaroxan did not interfere with guanabenz's protective effect (P. Tsaytler, H. P. Harding, D. Ron and A. Bertolotti, Science, 332, 1 Apr. 2011, 91-94). These observations demonstrate that guanabenz rescues cells from lethal ER stress by a mechanism independent of the α2-adrenergic receptor. Guanabenz protects cells from otherwise lethal accumulation of misfolded proteins by binding to a regulatory subunit of protein phosphatase 1, PPP1R15A (GADD34), selectively disrupting the stress-induced dephosphorylation of the α subunit of translation initiation factor 2 (eIF2α). Guanabenz sets the translation rates in stressed cells to a level manageable by available chaperones, thereby restoring protein homeostasis. It was reported that Guanabenz does not bind to the constitutive PPP1R15B (CReP) and therefore does not inhibit translation in non-stressed cells. (P. Tsaytler, H. P. Harding, D. Ron and A. Bertolotti, Science, 332, 1 Apr. 2011, 91-94).

Failure to maintain proteostasis in the ER by mounting an adequate unfolded protein response (UPR) is recognized as a contributing factor to many pathological conditions. Thus, the molecules described here, which inhibit eIF2α phosphatase to fine-tune protein synthesis, may be of therapeutic benefit to a large number of diseases caused protein misfolding stress and in particular with an accumulation of misfolded proteins.

The present invention seeks to provide alternative compounds based on a guanabenz core structure that have potential therapeutic applications in treating disorders associated with protein misfolding stress and in particular with an accumulation of misfolded proteins.

STATEMENT OF INVENTION

A first aspect of the invention relates to a compound of formula (I), or a pharmaceutically acceptable salt thereof,

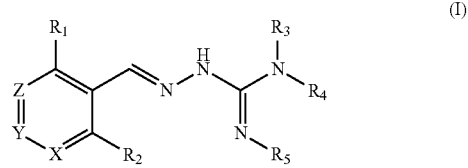

wherein:
$R_1$ is alkyl, Cl, F or Br;
$R_2$ is H or F;
$R_3$ is selected from H and alkyl;
$R_4$ is selected from H and $C(O)R_6$;
$R_5$ is H;
or $R_4$ and $R_5$ are linked to form a heterocyclic group which is optionally substituted with one or more $R_{10}$ groups;
$R_6$ is selected from $R_7$, $OR_7$, and $NR_8R_9$;
$R_7$, $R_8$ and $R_9$ are each independently selected from alkyl, cycloalkyl, aralkyl, cycloalkenyl, heterocyclyl and aryl, each of which is optionally substituted with one or more $R_{10}$ groups;

each $R_{10}$ is independently selected from halogen, OH, CN, COO-alkyl, aralkyl, $SO_2$-alkyl, $SO_2$-aryl, COOH, CO-alkyl, CO-aryl, $NH_2$, NH-alkyl, $N(alkyl)_2$, $CF_3$, alkyl and alkoxy;
X and Z are each independently $CR_{11}$, and Y is selected from $CR_{11}$ and N;
$R_{11}$ is H or F;
for use in treating a disorder associated with protein misfolding stress and in particular with an accumulation of misfolded proteins.

Previous studies have indicated that the aryl group must be at least disubstituted in order for the compounds to exhibit useful pharmacological activity (see for example, D. Tribouillard-Tanvier et al., PLoS One 3, e1981 (2008) and EP1908464A, CNRS). However, contrary to the results of previous studies, the present Applicant has surprisingly found that mono-substituted aryl derivatives are also active.

Moreover, compounds of formula (I) as defined above advantageously exhibit no activity toward the adrenergic α2A receptor relative to prior art compounds such as Guanabenz (FIG. 4). This loss in alpha-2 adrenergic activity renders the compounds therapeutically useful in the treatment of the disorders associated with protein misfolding stress and in particular with an accumulation of misfolded proteins, such as Charcot Marie Tooth (CMT), retinal diseases, preferably Retinitis Pigmentosa (RP), Alzheimer's disease, Parkinson's disease (PD), Amyotrophic Lateral Sclerosis (ALS), Huntington's disease, tauopathies, prion diseases, diabetes, preferably type 2 diabetes and cancer. The absence of alpha-2 adrenergic activity means that compounds of formula (I) can be administered at a dosage suitable to treat the aforementioned diseases, without any significant effect on blood pressure.

A second aspect of the invention relates to a compound of formula (II), or a pharmaceutically acceptable salt thereof,

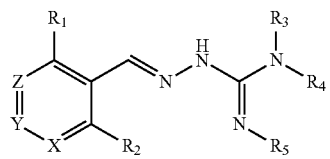

(II)

wherein:
$R_1$ is alkyl, Cl, F or Br;
$R_2$ is H or F;
$R_3$ is selected from H and alkyl;
$R_4$ is selected from H and $C(O)R_6$;
$R_5$ is H;
or $R_4$ and $R_5$ are linked to form a heterocyclic group which is optionally substituted with one or more $R_{10}$ groups;
$R_6$ is selected from $R_7$, $OR_7$, and $NR_8R_9$;
$R_7$, $R_8$ and $R_9$ are each independently selected from alkyl, cycloalkyl, aralkyl, cycloalkenyl, heterocyclic, aryl and heteroaryl, each of which is optionally substituted with one or more $R_{10}$ groups;
each $R_{10}$ is independently selected from halogen, OH, CN, COO-alkyl, aralkyl, $SO_2$-alkyl, $SO_2$-aryl, COOH, CO-alkyl, CO-aryl, $NH_2$, NH-alkyl, $N(alkyl)_2$, $CF_3$, alkyl and alkoxy;
X and Z are each independently $CR_{11}$, and Y is N;
$R_{11}$ is H or F.

A third aspect of the invention relates to a compound of formula (III), or a pharmaceutically acceptable salt thereof,

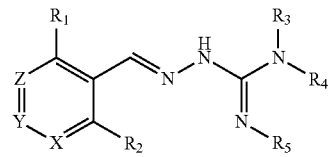

(III)

wherein:
$R_1$ is alkyl, Cl, F or Br;
$R_2$ is H or F;
$R_3$ is selected from H and alkyl;
$R_4$ is $C(O)R_6$;
$R_5$ is H;
or $R_4$ and $R_5$ are linked to form a heterocyclic group which is optionally substituted with one or more $R_{10}$ groups;
$R_6$ is selected from $R_7$, $OR_7$, and $NR_8R_9$;
$R_7$, $R_8$ and $R_9$ are each independently selected from alkyl, cycloalkyl, aralkyl, cycloalkenyl, heterocyclic, aryl and heteroaryl, each of which is optionally substituted with one or more $R_{10}$ groups;
each $R_{10}$ is independently selected from halogen, OH, CN, COO-alkyl, aralkyl, $SO_2$-alkyl, $SO_2$-aryl, COOH, CO-alkyl, CO-aryl, $NH_2$, NH-alkyl, $N(alkyl)_2$, $CF_3$, alkyl and alkoxy;
X and Z are each independently $CR_{11}$, and Y is selected from $CR_{11}$ and N; and
$R_{11}$ is H or F.

A fourth aspect of the invention relates to a compound of formula (IV), or a pharmaceutically acceptable salt thereof,

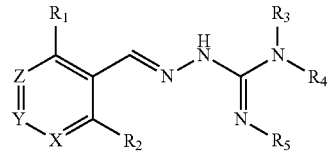

(IV)

wherein:
$R_1$ is alkyl or Br;
$R_2$ is H;
$R_3$ is selected from H and alkyl;
$R_4$ is selected from H and $C(O)R_6$;
$R_5$ is H;
or $R_4$ and $R_5$ are linked to form a heterocyclic group which is optionally substituted with one or more $R_{10}$ groups;
$R_6$ is selected from $R_7$, $OR_7$, and $NR_8R_9$;
$R_7$, $R_8$ and $R_9$ are each independently selected from alkyl, cycloalkyl, aralkyl, cycloalkenyl, heterocyclyl and aryl, each of which is optionally substituted with one or more $R_{10}$ groups;
each $R_{10}$ is independently selected from halogen, OH, CN, COO-alkyl, aralkyl, $SO_2$-alkyl, $SO_2$-aryl, COOH, CO-alkyl, CO-aryl, $NH_2$, NH-alkyl, $N(alkyl)_2$, $CF_3$, alkyl and alkoxy;
X and Z are each CH and Y is $CR_{11}$;
$R_{11}$ is H or F.

A further aspect of the invention relates to pharmaceutical compositions comprising a compound of formula (II), (III) or (IV) as described above, admixed with a suitable pharmaceutically acceptable diluent, excipient or carrier.

DETAILED DESCRIPTION

As used herein, the term "alkyl" includes both saturated straight chain and branched alkyl groups which may be substituted (mono- or poly-) or unsubstituted. Preferably, the alkyl group is a $C_{1-20}$ alkyl group, more preferably a $C_{1-15}$, more preferably still a $C_{1-12}$ alkyl group, more preferably still, a $C_{1-6}$ alkyl group, more preferably a $C_{1-3}$ alkyl group. Particularly preferred alkyl groups include, for example, methyl, ethyl, propyl, isopropyl, butyl, isobutyl, tert-butyl, pentyl and hexyl. Suitable substituents include, for example, one or more $R^{10}$ groups. Preferably, the alkyl group is unsubstituted.

As used herein, the term "cycloalkyl" refers to a cyclic alkyl group which may be substituted (mono- or poly-) or unsubstituted. Preferably, the cycloalkyl group is a $C_{3-12}$ cycloalkyl group. Suitable substituents include, for example, one or more $R^{10}$ groups.

As used herein, the term "alkenyl" refers to a group containing one or more carbon-carbon double bonds, which may be branched or unbranched, substituted (mono- or poly-) or unsubstituted. Preferably the alkenyl group is a $C_{2-20}$ alkenyl group, more preferably a $C_{2-15}$ alkenyl group, more preferably still a $C_{2-12}$ alkenyl group, or preferably a $C_{2-6}$ alkenyl group, more preferably a $C_{2-3}$ alkenyl group. Suitable substituents include, for example, one or more $R^{10}$ groups as defined above. The term "cyclic alkenyl" is to be construed accordingly.

As used herein, the term "aryl" refers to a $C_{6-12}$ aromatic group which may be substituted (mono- or poly-) or unsubstituted. Typical examples include phenyl and naphthyl etc. Suitable substituents include, for example, one or more $R^{10}$ groups.

As used herein, the term "heterocycle" (also referred to herein as "heterocyclyl" and "heterocyclic") refers to a substituted (mono- or poly-) or unsubstituted saturated, unsaturated or partially unsaturated cyclic group containing one or more heteroatoms selected from N, O and S, and which optionally further contains one or more CO groups. Suitable substituents include, for example, one or more $R^{10}$ groups. The term "heterocycle" encompasses both heteroaryl groups and heterocycloalkyl groups as defined below.

As used herein, the term "heteroaryl" refers to a $C_{2-12}$ aromatic, substituted (mono- or poly-) or unsubstituted group, which comprises one or more heteroatoms. Preferably, the heteroaryl group is a $C_{4-12}$ aromatic group comprising one or more heteroatoms selected from N, O and S. Suitable heteroaryl groups include pyrrole, pyrazole, pyrimidine, pyrazine, pyridine, quinoline, thiophene, 1,2,3-triazole, 1,2,4-triazole, thiazole, oxazole, iso-thiazole, iso-oxazole, imidazole, furan and the like. Again, suitable substituents include, for example, one or more $R^{10}$ groups.

As used herein, the term "heterocycloalkyl" refers to a substituted (mono- or poly-) or unsubstituted cyclic aliphatic group which contains one or more heteroatoms. Preferred heterocycloalkyl groups include piperidinyl, pyrrolidinyl, piperazinyl, thiomorpholinyl and morpholinyl. More preferably, the heterocycloalkyl group is selected from N-piperidinyl, N-pyrrolidinyl, N-piperazinyl, N-thiomorpholinyl and N-morpholinyl. Again, suitable substituents include, for example, one or more $R^{10}$ groups.

As used herein, the term "aralkyl" includes, but is not limited to, a group having both aryl and alkyl functionalities. By way of example, the term includes groups in which one of the hydrogen atoms of the alkyl group is replaced by an aryl group, e.g. a phenyl group optionally having one or more substituents such as halo, alkyl, alkoxy, hydroxy, and the like. Typical aralkyl groups include benzyl, phenethyl and the like.

In one preferred embodiment, $R_1$ is Cl, Br, Me or F, more preferably, Cl.

In one preferred embodiment, $R_2$ is H.

In one preferred embodiment, Y is $CR_{11}$.

In another preferred embodiment, Y is N.

In one preferred embodiment, $R_3$ and $R_4$ are both H.

In one preferred embodiment, $R_3$ is H and $R_4$ is $C(O)R_6$.

In one preferred embodiment, $R_6$ is alkyl or alkoxy, more preferably, Me or OMe.

In one preferred embodiment, $R_4$ and $R_5$ are linked to form a heterocyclic group which is optionally substituted with one or more $R_{10}$ groups.

In one preferred embodiment, said compound is of formula (Ia), or a pharmaceutically acceptable salt thereof,

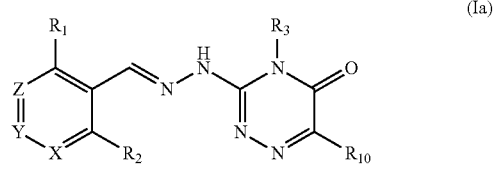

wherein $R_1$, $R_2$, $R_3$ and $R_{10}$ are as defined above.

In one especially preferred embodiment, the compound of formula (I) is selected from the following:

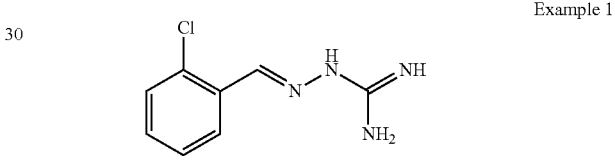

Example 1

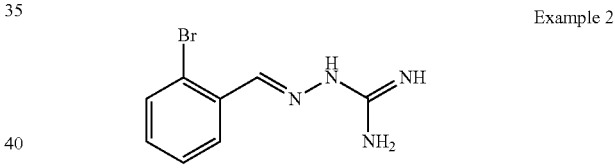

Example 2

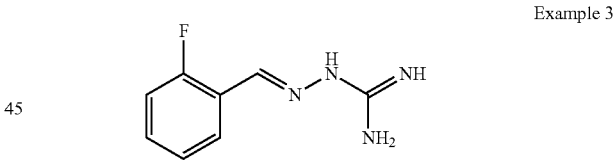

Example 3

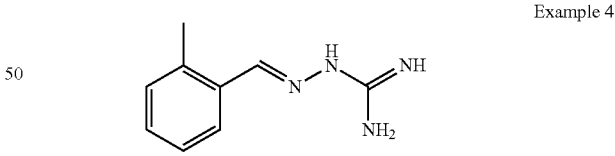

Example 4

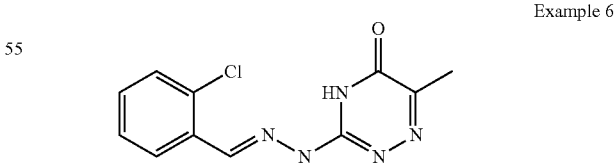

Example 6

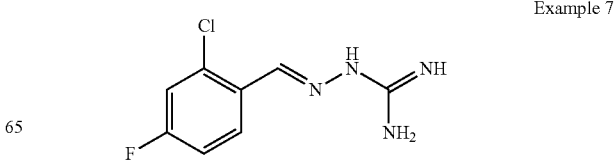

Example 7

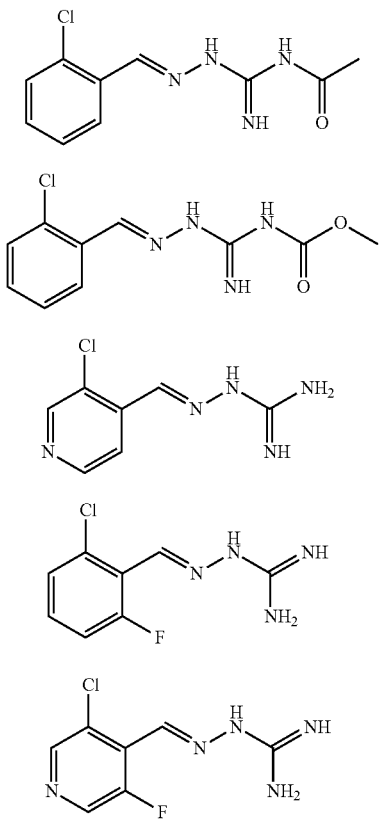

Example 8

Example 9

Example 13

Example 15

Example 16 and pharmaceutically acceptable salts thereof.

In one highly preferred embodiment, the compound of formula (I) is selected from Examples 1, 3, 6 and 15 as set out above.

Even more preferably, the compound of formula (I) is selected from Example 1 and Example 15, more preferably Example 1, i.e. the compound 1-[(E)-[(2-chlorophenyl)methylidene]amino]-guanidine.

Compounds

One aspect of the invention relates to compounds of formulae (II), (III) or (IV), or pharmaceutically acceptable salts thereof, as defined above. Preferred aspects of the invention apply mutatis mutandis. Particularly preferred compounds for this aspect of the invention include Examples 7, 8, 9, 13 and 16 as described herein.

Therapeutic Applications

The Applicant has demonstrated that compounds of formula (I) have potential therapeutic applications in treating disorders associated with accumulation of misfolded proteins. In particular, compounds of formula (I) have been shown to have a protective effect against cytotoxic endoplasmic reticulum (ER) stress and age related disorders.

Another aspect of the invention relates to the use of a compound of formula (I) as defined above in the preparation of a medicament for treating a disorder associated with protein misfolding stress and in particular with an accumulation of misfolded proteins.

As used herein the phrase "preparation of a medicament" includes the use of one or more of the above described compounds directly as the medicament in addition to its use in a screening programme for further active agents or in any stage of the manufacture of such a medicament.

Yet another aspect of the invention relates to a method of treating a disorder associated with protein misfolding stress and in particular with an accumulation of misfolded proteins in a subject in need thereof, said method comprising administering a therapeutically effective amount of a compound of formula (I) as defined above to said subject.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Herein, the term "treating" includes abrogating, substantially inhibiting, slowing or reversing the progression of a disease or disorder, substantially ameliorating clinical symptoms of a disease or disorder or substantially preventing the appearance of clinical symptoms of a disease or disorder.

The term "therapeutically effective amount" refers to that amount of the compound being administered which will relieve to some extent one or more of the symptoms of the disease or disorder being treated.

The unfolded protein response (UPR) is a component of the cellular defense system against misfolded proteins that adapts folding in the endoplasmic reticulum (ER) to changing conditions. The UPR is activated in response to an accumulation of unfolded or misfolded proteins in the lumen of the endoplasmic reticulum. In this scenario, the UPR has two primary aims: (i) to restore normal function of the cell by halting protein translation, and (ii) to activate the signaling pathways that lead to the increased production of molecular chaperones involved in protein folding. If these objectives are not achieved within a certain time frame, or the disruption is prolonged, the UPR aims towards apoptosis.

Upstream components of the UPR are the ER-resident trans-membrane proteins IRE1, ATF6, and PERK, which sense folding defects to reprogram transcription and translation in a concerted manner and restore proteostasis. Activated IRE1 and ATF6 increase the transcription of genes involved in ER folding, such as those encoding the chaperones BiP and GRP94. Activated PERK attenuates global protein synthesis by phosphorylating the subunit of translation initiation factor 2 (eIF2α) on Ser51 while promoting translation of the transcription factor ATF4. The latter controls expression of CHOP, another transcription factor, which in turn promotes expression of PPP1R15A/GADD34. PPP1R15A, an effector of a negative feedback loop that terminates UPR signaling, recruits a catalytic subunit of protein phosphatase 1 (PP1c) to dephosphorylate eIF2α, allowing protein synthesis to resume. UPR failure contributes to many pathological conditions that might be corrected by adequate boost of this adaptive response. Selective inhibitors of the stressed-induced eIF2α phosphatase PPP1R15A-PP1 delays eIF2α dephosphorylation and consequently protein synthesis selectively in stressed cells, without affecting protein synthesis in unstressed cells. This prolongs the beneficial effects of the UPR. A transient reduction of protein synthesis is beneficial to stressed cells because decreasing the flux of proteins synthesized increases the availability of chaperones and thus protects from misfolding stress (P. Tsaytler, H. P. Harding, D. Ron and A. Bertolotti, Science, 332, 1 April 2011, 91-94). Non-selective inhibitors of the 2 eIF2α phosphatases might have undesirable effects, as persistent translation inhibition is deleterious. Indeed, genetic ablation of both PPP1R15A and PPP1R15B results in early embryonic lethality in mice indicating that inhibition of the two eIF2α phosphatases PPP1R15A-PP1 and PPP1R15B-PP1 is deleterious in an organismal context. In contrast, genetic ablation of PPP1R15A has no harmful consequence in mice (Harding et al., 2009, Proc Natl Acad Sci USA, 106, 1832-1837). Furthermore, specific inhibitors of PPP1R15A are predicted to be inert in unstressed cells, as the PPP1R15A is not expressed in absence of stress. Thus, selective PPP1R15A inhibitors are predicted to be safe. Non-selective inhibitors of the two eIF2α phosphatases may also be useful to treat protein misfolding diseases, when used at doses that result in only a partial inhibition of the phosphatases.

Cytoprotection against ER stress can be measured by a suitable assay. For example, cytoprotection can be measured in HeLa cells in which ER stress is elicited by the addition of media containing tunicamycin, a mixture of homologous nucleoside antibiotics that inhibits the UDP-HexNAc: polyprenol-P HexNAc-1-P family of enzymes and is used to induce unfolded protein response. Cell viability can be detected in the presence and absence of inhibitor compounds after a set period of time, by measuring the reduction of WST-8 into formazan using a standard cell viability kit (such as Cell Viability Counting Kit-8 from Dojindo). Cytoprotection from ER stress is measured in terms of the percentage increase in viable cells (relative to control) after ER stress. Further details of a suitable assay are set forth in the accompanying Examples section.

In one preferred embodiment, the compound of formula (I) is capable of prolonging the protective effect of the UPR relative to the control (i.e. in the absence of inhibitor compound) by at least 20%, more preferably, at least 30%, even more preferably, at least 40%, at least 50%, at least 60%, at least 70%, at least 80%, more preferably still, at least 90%.

The Applicant has demonstrated that compounds of formula (I) are inhibitors of PPP1R15A-PP1 interaction which induce a protective effect. Preferably, the compound exhibits a protective effect with $EC_{50}$ of less than about 5 µM, even more preferably, less than about 2 µM, more preferably still, less than about 1 µM. The compound should preferably be devoid of alpha2 adrenergic activity. Thus, in one preferred embodiment the compound does not exhibit any activity in a functional alpha-2-adrenergic assay.

The Applicant has further demonstrated that certain compounds of formula (I) selectively inhibit PPP1R15A-PP1, and thus prolong the protective effect of the UPR, thereby rescuing cells from protein misfolding stress. Inhibitors of PPP1R15A-PP1 described in the present invention therefore have therapeutic applications in the treatment of a variety of diseases associated with protein misfolding stress and in particular with an accumulation of misfolded proteins.

In one embodiment, the compound of formula (I) is capable of inhibiting PPP1R15A and PPP1R15B.

In one preferred embodiment, the compound of formula (I) is capable of selectively inhibiting PPP1R15A over PPP1R15B.

In one preferred embodiment of the invention, the compound of formula (I) is for use in treating neurodegenerative diseases, and more specifically where accumulation of misfolded proteins is involved in the mode of action (Brown et al, 2012, Frontiers in Physiology, 3, Article 263).

In one particularly preferred embodiment, the compound of formula (I) is for use in treating a disorder selected from Charcot Marie Tooth, severe Dejerine-Sottas syndrome (Voermans et al., 2012, J Peripher New Syst, 17(2), 223-5), a retinal disease (such as but not restricted to retinitis pigmentosa, retinal ciliopathies, macular degeneration, diabetic retinopathy), Alzheimer's disease, Parkinson's disease, Amyotrophic Lateral Sclerosis (ALS), Huntington's disease, tauopathies, prion diseases, type 2 diabetes and/or type 1 diabetes and cancer, such as but not restricted to, multiple myeloma.

In one embodiment, the invention relates to a compound of formula (I) as defined above for use in treating a disorder associated with the eIF2α phosphorylation pathway where accumulation of misfolded proteins is involved in the mode of action. Preferably, the disorder is a PPP1R15A-related disease or disorder. Examples of such disorders include protein misfolding diseases, such as but not limited to, Charcot Marie Tooth, severe Dejerine-Sottas syndrome and Retinitis pigmentosa.

In another embodiment, the invention relates to a compound of formula (I) as defined above for use in treating a disorder caused by, associated with or accompanied by eIF2α phosphorylation and/or PPP1R15A activity where accumulation of misfolded proteins is involved in the mode of action.

In another embodiment, the invention relates to a compound of formula (I) as defined above for use in treating UPR disorder such as, but not limited to aging (Naidoo et al., 2008, J Neurosci, 28, 6539-48).

As used herein, "PPP1R15A related disease or disorder" refers to a disease or disorder characterized by abnormal PPP1R15A activity where accumulation of misfolded proteins is involved in the mode of action. Abnormal activity refers to: (i) PPP1R15A expression in cells which normally do not express PPP1R15A; (ii) increased PPP1R15A expression; or, (iii) increased PPP1R15A activity.

In another embodiment, the invention relates to a method of treating a mammal having a disease state alleviated by the inhibition of PP1R15A, where accumulation of misfolded proteins is involved in the mode of action, wherein the method comprises administering to a mammal a therapeutically effective amount of a compound of formula (I) as defined above.

In another embodiment, the invention relates to a PPP1R15A inhibitor of formula (I) or a pharmaceutical acceptable salt thereof for the use in treating disorders associated with protein misfolding stress and in particular with an accumulation of misfolded proteins and/or UPR disorders, wherein said compound has no or reduced adrenergic alpha 2 agonist activity in comparison with Guanabenz.

In another embodiment, the invention relates to a PPP1R15A inhibitor of formula (I) or a pharmaceutical acceptable salt thereof for the use in treating disorders associated with protein misfolding stress and in particular with an accumulation of misfolded proteins and/or UPR disorders, wherein said compound does not inhibit protein translation in non-stressed cells expressing PPP1R15B.

In another embodiment, the invention relates to a method of treating a disorder characterized by ER stress response activity with an accumulation of misfolded proteins, the method comprising administering to a patient a therapeutically effective amount of at least one compound of formula (I) wherein said compound modulates ER stress response.

In another embodiment, the invention relates to PPP1R15A inhibitor of formula (I) or a pharmaceutical acceptable salt thereof for the use in treating disorders associated with protein misfolding stress and in particular with an accumulation of misfolded proteins and/or UPR disorders, wherein said compound has a selectivity towards PPP1R15A-PP1 holophosphatase, having but no or reduced activity towards PPP1R15B-PP1 holophosphatase, and wherein the ratio (activity towards PPP1R15A-PP1 holophosphatase/activity towards PPP1R15B-PP1) for said compound is at least equal or superior to the ratio (activity towards PPP1R15A-PP1 holophosphatase/activity towards PPP1R15B-PP1) for Guanabenz.

In another embodiment, the invention relates to a PPP1R15A inhibitor of formula (I) or a pharmaceutical acceptable salt thereof for the use in treating disorders associated with protein misfolding stress and in particular with an accumulation of misfolded proteins and/or UPR disorders, wherein:
 said compound has an activity towards PPP1R15A-PP1 holophosphatase but no or reduced activity towards PPP1R15B-PP1 holophosphatase, and;
 wherein the ratio (activity towards PPP1R15A-PP1 holophosphatase/activity towards PPP1R15B-PP1) for said compound is at least equal or superior to the ratio (activity towards PPP1R15A-PP1 holophosphatase/activity towards PPP1R15B-PP1) for Guanabenz; and
 wherein said compound has no or reduced adrenergic alpha 2 agonist activity in comparison with Guanabenz.

As used herein, the disease or disorder characterized by ER stress response activity, and/or the disease or disorder associated with protein misfolding stress and in particular with an accumulation of misfolded proteins and/or UPR disorders, is selected from Charcot Marie Tooth, severe Dejerine-Sottas syndrome (Voermans et al., 2012, J Peripher New Syst, 17(2), 223-5), a retinal disease (such as but not restricted to retinitis pigmentosa, retinal ciliopathies, macular degeneration, diabetic retinopathy), Alzheimer's disease, Parkinson's disease, Amyotrophic Lateral Sclerosis (ALS), Huntington's disease, diabetes, such as but not restricted to type 2 diabetes and cancer such as but not restricted to multiple myeloma.

Charcot Marie Tooth

In one preferred embodiment, the compound of formula (I) is for use in treating Charcot Marie Tooth.

Over a 100 mutations in the gene encoding myelin protein zero (P0), a single-pass transmembrane protein, which is the major protein produced by myelinating Schwann cells causes Charcot-Marie-Tooth neuropathy (D'Antonio et al., 2009, J Neurosci Res, 87, 3241-9). The mutations are dominantly inherited and cause the disease through a gain of toxic function (D'Antonio et al., 2009, J Neurosci Res, 87, 3241-9). Deletion of serine 63 from P0 (P0S63del) causes Charcot-Marie-Tooth 1B neuropathy in humans and a similar demyelinating neuropathy in transgenic mice. The mutant protein accumulates in the ER and induces the UPR (D'Antonio et al., 2009, J Neurosci Res, 87, 3241-9). Genetic ablation of CHOP, a pro-apoptotic gene in the UPR restores motor function in Charcot-Marie-Tooth mice (Pennuto et al., 2008, Neuron, 57, 393-405). The finding that PPP1R15A inhibition in cells nearly abolishes CHOP expression in ER-stressed cells indicates that genetic or pharmacological inhibition of PPP1R15A should reduce motor dysfunction in Charcot-Marie-Tooth mice. Recently, D'Antonio et al. (2013 J. Exp. Med Vol. pp 1-18) demonstrated that P0S63del mice treated with salubrinal, a small molecule that increases the phosphorylation of eIF2alpha (Boyce et al. 2005 Science Vol. 307 pp 935-939) regained almost normal motor capacity in rotarod analysis and was accompanied by a rescue of morphological and electrophysiological abnormalities. Accumulation of the of CMT-related mutant in the ER proteins is not unique to P0S63del; at least five other P0 mutants have been identified that are retained in the ER and elicit an UPR (Pennuto et al., 2008 Neuron Vol. 57 pp 393-405; Saporta et al., 2012 Brain Vol. 135 pp 2032-2047). In addition, protein misfolding and accumulation of misfolded protein in the ER have been implicated in the pathogenesis of other CMT neuropathies as a result of mutations in PMP22 and Cx32 (Colby et al., 2000 Neurobiol. Disease Vol. 7 pp 561-573; Kleopa et al., 2002 J. Neurosci. Res. Vol. 68 pp 522-534; Yum et al., 2002 Neurobiol. Dis. Vol. 11 pp 43-52). However, Salubrinal is toxic and can not be used to treat human patients D'Antonio et al. (2013 J. Exp. Med Vol. pp 1-18). In contrast, the PPP1R15A inhibitors of formula (I) are predicted to be safe and could be useful for the treatment of CMT-1A and 1B.

Retinal Diseases

Recently Published Literature has Provided Evidences that the UPR is Involved in the development of retinal degeneration: inherited retinal degeneration such as retinal ciliopathies & retinitis pigmentosa, macular degeneration, retinopathy of prematurity, light-induced retinal degeneration, retinal detachment, diabetic retinopathy and glaucoma (for review Gorbatyuk et Gorbatyuk 2013—Retinal degeneration: Focus on the unfolded protein response, Molecular Vision Vol. 19 pp 1985-1998).

In one preferred embodiment, the compound of formula (I) is for use in treating retinal diseases, more preferably, inherited retinal degeneration such as retinal ciliopathies & retinitis pigmentosa, macular degeneration, retinopathy of prematurity, light-induced retinal degeneration, retinal detachment, diabetic retinopathy and glaucoma.

Retinal ciliopathies are a group of rare genetic disorders originating from a defect in the primary cilium of photoreceptors thus inducing retinitis pigmentosa. This defect has been reported to induce an ER stress due to protein accumulation in the inner segment of the photoreceptor which in turn induces the UPR (WO2013/124484). Retinal degeneration is a very common feature in ciliopathies that can be observed either in isolated retinitis pigmentosa such as Leber's congenital amaurosis or X-linked retinitis pigmentosa, or also in syndromic conditions like the Bardet-Biedl Syndrome (BBS) or the Alström syndrome (ALMS). The retinal ciliopathy is selected from the group consisting of Bardet-Biedl syndrome, Senior-Loken syndrome, Joubert syndrome, Salidono-Mainzer syndrome, Sensenbrenner syndrome, Jeune syndrome, Meckel-Gruder syndrome, Alstrôm syndrome, MORM syndrome, Leber's congenital amaurosis caused by mutation in a ciliary gene and X-linked retinitis pigmentosa caused by mutation in the RPGR gene.

Retinitis pigmentosa is an inherited, degenerative eye disease that causes severe vision impairment and often blindness. It is the most common cause of genetically determined blindness. Sufferers will experience one or more of the following symptoms: night blindness; tunnel vision (no peripheral vision); peripheral vision (no central vision); latticework vision; aversion to glare; slow adjustment from dark to light environments and vice versa; blurring of vision; poor color separation; and extreme tiredness.

Emerging evidence supports a role of ER stress in retinal apoptosis and cell death (Jing et al., 2012, Exp Diabetes Res, 2012, 589589). Retinis pigmentosa (RP) is the most common form of hereditary retinal degeneration caused by over 100 mutations in the rhodopsin gene (Dryja et al., 1991, Proc Natl Acad Sci USA, 88, 9370-4). Rhodopsin is a G protein-coupled receptor that transduces light in the rod photoreceptors and consists of a covalent complex between the transmembrane protein opsin of 348 amino acids, covalently bound to 11-cis retinal (Palczewski, 2006, Annu Rev Biochem, 75, 743-67). The RP-causing rhodopsin mutations are mostly missense mutations distributed throughout the protein (Dryja et al., 1991, Proc Natl Acad Sci USA, 88, 9370-4), similar to the ALS-causing SOD1 mutations (Valentine et al., 2005, Annu Rev Biochem, 74, 563-93). The RP-causing rhodopsin mutants have been studied in diverse systems and results from heterologous expression of the proteins in mammalian cells, in transgenic mice and drosophila are consistent (Griciuc et al., 2011, Trends Mol Med, 17, 442-51). The most prevalent RP-causing rhodopsin are misfolded, do not bind 11-cis-retinal, do not reach the cell surface but are retained in the ER (Griciuc et al., 2011, Trends Mol Med, 17, 442-51). Misfolding of the rhodopsin mutants causes ER stress and rod cell death (Griciuc et al., 2011, Trends Mol Med, 17, 442-51). This strongly suggests that the PPP1R15A inhibitors described in the invention will be useful to treat RP.

Age-related macular degeneration (AMD) is the main cause of legal blindness among those over 65 years of age in the United States. AMD was reported to account for 54% of all current cases of blindness among the Caucasian population in the United States. The study predicted that as a result of the rising prevalence of AMD, the number of blind people in the US could increase by as much as 70% by 2020.

Shen et al. (2011 Effect of Guanabenz on Rat AMD Models and Rabbit Choroidal Blood—Vol. 5 pp 27-31) demonstrated that Guanabenz significantly protected retinal pigment epithelium (RPE) from NaIO3-induced degeneration, inhibited the development of choroidal neovascularization (CNV) in laser-induced rat AMD model and increased choroidal blood flow markedly in vivo.

However. Guanabenz is an alpha2 adrenergic receptor and because of its hypotensive activity, it can not be used to treat retinal or macular degeneration.

Compounds of the invention which are PPP1R15A inhibitors like Guanabenz but which advantageously exhibit no activity toward the adrenergic alpha2A receptor will ameliorate retinal or macular.

Alzheimer's Disease, Parkinson's Disease, ALS, Huntington's Disease, Tauopathies and Prion Diseases In one preferred embodiment, the compound of formula (I) is for use in treating a disease selected from Alzheimer's disease, Parkinson's disease, ALS, Huntington's disease, tauopathies and prion diseases.

Because accumulation of misfolded proteins is a hallmark of diverse diseases and having shown that compound of formula (I) reduces accumulation of 4 unrelated misfolded and disease-causing proteins (FIG. 4-6), the compound of formula (I) will be useful to also treat other neurodegenerative diseases caused by accumulation of misfolded proteins.

In addition, as UPR induction is a hallmark of these diseases caused by accumulation of misfolded protein, the compound of formula (I) will be useful to treat these diseases. (Scheper & Hoozemans 2009; Kim et al. 2008).

Guanabenz reduces the symptoms of prion infected mice (D. Tribouillard-Tanvier et al., 2008 PLoS One 3, e1981). However, Guanabenz is not useful for the treatment of human protein misfolding diseases due to its hypotensive activity. In contrast, the PPP1R15A inhibitors, devoid of alpha2 adrenergic activity, and described in this invention could be useful to treat prion diseases.

Parkinson's Disease (PD)

Salubrinal inhibits the PPP1R15A mediated dephosphorylation of eIF2α (Boyce et al. 2005 Science Vol. 307 pp 935-939). Recently, Colla et al. (J. of Neuroscience 2012 Vol. 32 N° 10 pp 3306-3320) demonstrated that Salubrinal significantly attenuates disease manifestations in two animal models of alpha-synucleinopathy.

Without to be bound by a theory, it is anticipated that compounds of the invention which are PPP1R15A inhibitors will ameliorate disease manifestations of alpha-syncleinopathies such as Parkinson's disease.

Amyotrophic Lateral Sclerosis (ALS)

Saxena et al. (Nature Neuroscience 2009 Vol. 12 pp 627-636) demonstrated that Salubrinal extends the life span of a G93A-SOD1 transgenic mouse model of motor neuron disease. Without to be bound by a theory, it is anticipated that compounds of the invention which are PPP1R15A inhibitors will ameliorate disease manifestations of ALS with the SOD1 mutation G93A. More than 140, mostly missense, mutations in the SOD1 gene cause aggregation of the affected protein in familial forms of amyotrophic lateral sclerosis (ALS). Because diverse SOD1 mutants share common defects (Munch et al. 2010), it is accepted that diverse SOD1 mutant cause ALS by a common mechanism. Moreover, the clinical manifestations are shared between sporadic and familial forms of the diseases, and it is now well recognized that protein misfolding plays a central role in both familial and sporadic ALS. Therefore, the compounds of formula (I) can be used to treat both familial and sporadic forms of ALS.

The Applicant has found that the cytoprotective activity of guanabenz on protein misfolding stress is surprisingly broad as guanabenz also reduces mutant huntingtin accumulation in cells (WO 2008/041133). This finding is unexpected since mutant huntingtin is either cytosolic or nuclear. However, there is evidence that mutant huntingtin metabolism has previously been connected to the ER stress response (Nishitoh et al., 2002, Genes Dev, 16, 1345-55; Rousseau et al., 2004, Proc Natl Acad Sci USA, 101, 9648-53; Duennwald and Lindquist, 2008, Genes Dev, 22, 3308-19). The Applicant's findings that guanabenz protects cells from cytotoxic ER stress and reduces mutant huntingtin accumulation further supports the idea that there may be aspects of the ER stress response that impact on mutant huntingtin accumulation. Furthermore, dysfunction of the ER stress response has been involved in a variety of pathologies, including type 2 diabetes and neurodegeneration (Scheper and Hoozemans, 2009, Curr Med Chem, 16, 615-26). Thus, without wishing to be bound by theory, it is believed that guanabenz and related compounds have a protective effect against secondary UPR disorders, namely disorders due to an accumulation of a non-ER resident misfolded protein, which induces the UPR.

Diabetes

In one preferred embodiment, the compound of formula (I) is for use in treating diabetes, more preferably type 2 diabetes.

The insulin-secreting β-cells in the pancreas have a heavy and tightly regulated biosynthetic burden consisting in insulin secretion. Thus, these cells have an important need to maintain ER homeostasis (Back and Kaufman, 2012, Annu Rev Biochem, 81, 767-93). Type 2 diabetes is manifested by increased levels of blood glucose due to insulin resistance in the adipose, muscle and liver and/or impaired insulin secretion from pancreatic β-cells. As a response, β-cells mass increase and their function is enhanced. Eventually, the burden on the β-cells is too high leading to their progressive decline and death. Increasing evidence reveals that death of β-cells results from ER stress (Back and Kaufman, 2012, Annu Rev Biochem, 81, 767-93). Importantly, Chop deletion improves β-cells function in diverse models of diabetes (Song et al., 2008, J Clin Invest, 118, 3378-89). Without wishing to be bound by theory, it is believed that inhibitors of PPP1R15A-PP1 will improve β-cells function in type 2 diabetes since inhibition of PPP1R15A-PP1 reduces the levels of the pro-apoptotic protein CHOP during ER stress (Tsaytler et al., 2011, Science, 332, 91-4).

Cancer

In one preferred embodiment, the compound of formula (I) is for use in treating cancer.

Cancer cells have high metabolic requirement and their proliferation relies on efficient protein synthesis. Translation initiation plays a crucial role in controlling protein homeostasis, differentiation, proliferation and malignant transformation. Increasing translation initiation contributes to cancer initiation and conversely, decreasing translation initiation could reduce tumor growth (Donze et al., 1995, EMBO J, 14, 3828-34; Pervin et al., 2008, Cancer Res, 68, 4862-74; Chen et al., 2011, Nat Chem Biol, 7, 610-6). Without wishing to be bound by theory, it is believed that inhibiting PPP1R15A could selectively reduce translation in tumor cells and thus reduce tumor growth.

Aging

Aging is known to impair stress responses and in particular, the UPR is impaired with age (Naidoo et al., 2008, J Neurosci, 28, 6539-48). Thus, prolonging the beneficial effect of the UPR by inhibition of eIF2α phosphatase could ameliorate age-related disorders.

Pharmaceutical Compositions

For use according to the present invention, the compounds or physiologically acceptable salts, esters or other physiologically functional derivatives thereof, described herein, may be presented as a pharmaceutical formulation, comprising the compounds or physiologically acceptable salt, ester or other physiologically functional derivative thereof, together with one or more pharmaceutically acceptable carriers therefore and optionally other therapeutic and/or prophylactic ingredients. The carrier(s) must be acceptable in the sense of being compatible with the other ingredients of the formulation and not deleterious to the recipient thereof. The pharmaceutical compositions may be for human or animal usage in human and veterinary medicine.

Examples of such suitable excipients for the various different forms of pharmaceutical compositions described herein may be found in the "Handbook of Pharmaceutical Excipients, 2$^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s), buffer(s), flavouring agent(s), surface active agent(s), thickener(s), preservative(s) (including anti-oxidants) and the like, and substances included for the purpose of rendering the formulation isotonic with the blood of the intended recipient.

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Pharmaceutical formulations include those suitable for oral, topical (including dermal, buccal, ocular and sublingual), rectal or parenteral (including subcutaneous, intradermal, intramuscular and intravenous), nasal, intra-ocularly and pulmonary administration e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release-controlling matrix, or is coated with a suitable release-controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds.

Pharmaceutical formulations suitable for parenteral administration include sterile solutions or suspensions of an active compound in aqueous or oleaginous vehicles.

Pharmaceutical formulations of the invention are suitable for ophthalmic administration, in particular for intra-ocular, topical ocular or peri-ocular administration, more preferably for topical ocular or peri-ocular administration.

Injectible preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient. As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microliters, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

According to a further aspect of the invention, there is provided a process for the preparation of a pharmaceutical or veterinary composition as described above, the process comprising bringing the active compound(s) into association with the carrier, for example by admixture.

In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) in conjunction or association with a pharmaceutically or veterinarily acceptable carrier or vehicle.

Salts/Esters

The compounds of the invention can be present as salts or esters, in particular pharmaceutically and veterinarily acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. hydrohalic acids such as hydrochloride, hydrobromide and hydroiodide, sulfuric acid, phosphoric acid sulphate, bisulphate, hemisulphate, thiocyanate, persulphate and sulphonic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Salts which are not pharmaceutically or veterinarily acceptable may still be valuable as intermediates.

Preferred salts include, for example, acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers, diastereoisomers and tautomers of the compounds of the invention. The person skilled in the art will recognise compounds that possess optical properties (one or more chiral carbon atoms) or tautomeric characteristics. The corresponding enantiomers and/or tautomers may be isolated/prepared by methods known in the art. Enantiomers are characterised by the absolute configuration of their chiral centres and described by the R- and S-sequencing rules of Cahn, Ingold and Prelog. Such conventions are well known in the art (e.g. see 'Advanced Organic Chemistry', $3^{rd}$ edition, ed. March, J., John Wiley and Sons, New York, 1985).

Compounds of formula (I) thus also include the tautomer forms of formula:

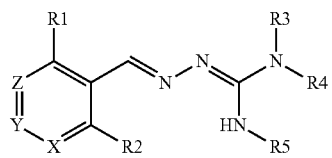

As an illustrative example, a tautomer form of example 1 is:

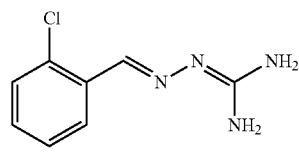 [SMILES: NC(N)=N/N=C/c1ccccc1Cl]

Compounds of the invention containing a chiral centre may be used as a racemic mixture, an enantiomerically enriched mixture, or the racemic mixture may be separated using well-known techniques and an individual enantiomer may be used alone.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulfur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. For example, the invention includes compounds of general formula (I) where any hydrogen atom has been replaced by a deuterium atom. Isotopic variations of the agent of the present invention and pharmaceutically acceptable salts thereof of this invention can generally be prepared by conventional procedures using appropriate isotopic variations of suitable reagents.

Prodrugs

The invention further includes the compounds of the present invention in prodrug form, i.e. covalently bonded compounds which release the active parent drug according to general formula (I) in vivo. Such prodrugs are generally compounds of the invention wherein one or more appropriate groups have been modified such that the modification may be reversed upon administration to a human or mammalian subject. Reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Solvates

The present invention also includes solvate forms of the compounds of the present invention. The terms used in the claims encompass these forms.

Polymorphs

The invention further relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Administration

The pharmaceutical compositions of the present invention may be adapted for rectal, nasal, intrabronchial, topical (including buccal, sublingual and ophthalmic administration, in particular for intra-ocular, topical ocular or peri-ocular administration), vaginal or parenteral (including subcutaneous, intramuscular, intravenous, intraarterial and intradermal), intraperitoneal or intrathecal administration. Preferably the formulation is an orally administered formulation. The formulations may conveniently be presented in unit dosage form, i.e., in the form of discrete portions containing a unit dose, or a multiple or sub-unit of a unit dose. By way of example, the formulations may be in the form of tablets and sustained release capsules, and may be prepared by any method well known in the art of pharmacy.

Formulations for oral administration in the present invention may be presented as: discrete units such as capsules, gellules, drops, cachets, pills or tablets each containing a predetermined amount of the active agent; as a powder or granules; as a solution, emulsion or a suspension of the active agent in an aqueous liquid or a non-aqueous liquid; or as an oil-in-water liquid emulsion or a water-in-oil liquid emulsion; or as a bolus etc. Preferably, these compositions contain from 1 to 250 mg and more preferably from 10-100 mg, of active ingredient per dose.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Other forms of administration comprise solutions or emulsions which may be injected intravenously, intraarterially, intrathecally, subcutaneously, intradermally, intraperitoneally, intra-ocularly, topical, peri-ocularly or intramuscularly, and which are prepared from sterile or sterilisable solutions. Injectable forms typically contain between 10-1000 mg, preferably between 10-250 mg, of active ingredient per dose.

The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

In accordance with this invention, an effective amount of a compound of general formula (I) may be administered to target a particular condition or disease. Of course, this dosage amount will further be modified according to the type of administration of the compound. For example, to achieve an "effective amount" for acute therapy, parenteral administration of a compound of general formula (I) is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at an effective concentration The compounds may be administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect.

The compounds of this invention may also be administered orally to the patient, in a manner such that the concentration of drug is sufficient to achieve one or more of the therapeutic indications disclosed herein. Typically, a pharmaceutical composition containing the compound is administered at an oral dose of between about 0.1 to about 50 mg/kg in a manner consistent with the condition of the patient. Preferably the oral dose would be about 0.1 to about 20 mg/kg.

No unacceptable toxicological effects are expected when compounds of the present invention are administered in accordance with the present invention. The compounds of this invention, which may have good bioavailability, may be tested in one of several biological assays to determine the concentration of a compound which is required to have a given pharmacological effect.

Combinations

In a particularly preferred embodiment, the one or more compounds of the invention are administered in combination with one or more other active agents, for example, existing drugs available on the market. In such cases, the compounds of the invention may be administered consecutively, simultaneously or sequentially with the one or more other active agents.

Drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining drugs are that it may promote additive or possible synergistic effects through biochemical interactions and also may decrease the emergence of resistance.

Beneficial combinations may be suggested by studying the inhibitory activity of the test compounds with agents known or suspected of being valuable in the treatment of a particular disorder. This procedure can also be used to determine the order of administration of the agents, i.e. before, simultaneously, or after delivery. Such scheduling may be a feature of all the active agents identified herein.

Assay

A further aspect of the invention relates to the use of a compound as described above in an assay for identifying further candidate compounds capable of inhibiting PPP1R15A-PP1.

Preferably, the assay is a competitive binding assay.

More preferably, the competitive binding assay comprises contacting a compound of the invention with PPP1R15A-PP1 and a candidate compound and detecting any change in the interaction between the compound according to the invention and the PPP1R15A-PP1.

Preferably, the candidate compound is generated by conventional SAR modification of a compound of the invention.

As used herein, the term "conventional SAR modification" refers to standard methods known in the art for varying a given compound by way of chemical derivatisation.

Thus, in one aspect, the identified compound may act as a model (for example, a template) for the development of other compounds. The compounds employed in such a test may be free in solution, affixed to a solid support, borne on a cell surface, or located intracellularly. The abolition of activity or the formation of binding complexes between the compound and the agent being tested may be measured.

The assay of the present invention may be a screen, whereby a number of agents are tested. In one aspect, the assay method of the present invention is a high through-put screen.

This invention also contemplates the use of competitive drug screening assays in which neutralising antibodies capable of binding a compound specifically compete with a test compound for binding to a compound.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

Preferably, the competitive binding assay comprises contacting a compound of the invention with PPP1R15A-PP1 in the presence of a known substrate of PPP1R15A-PP1 and detecting any change in the interaction between said PPP1R15A-PP1 and said known substrate.

A further aspect of the invention provides a method of detecting the binding of a ligand to PPP1R15A-PP1, said method comprising the steps of:
(i) contacting a ligand with PPP1R15A-PP1 in the presence of a known substrate
(ii) detecting any change in the interaction between PPP1R15A-PP1 and said known substrate;
and wherein said ligand is a compound of the invention.

One aspect of the invention relates to a process comprising the steps of:
(a) performing an assay method described hereinabove;
(b) identifying one or more ligands capable of binding to a ligand binding domain; and
(c) preparing a quantity of said one or more ligands.

Another aspect of the invention provides a process comprising the steps of:
(a) performing an assay method described hereinabove;
(b) identifying one or more ligands capable of binding to a ligand binding domain; and
(c) preparing a pharmaceutical composition comprising said one or more ligands.

Another aspect of the invention provides a process comprising the steps of:
(a) performing an assay method described hereinabove;
(b) identifying one or more ligands capable of binding to a ligand binding domain;
(c) modifying said one or more ligands capable of binding to a ligand binding domain;
(d) performing the assay method described hereinabove;
(e) optionally preparing a pharmaceutical composition comprising said one or more ligands.

The invention also relates to a ligand identified by the method described hereinabove.

Yet another aspect of the invention relates to a pharmaceutical composition comprising a ligand identified by the method described hereinabove.

Another aspect of the invention relates to the use of a ligand identified by the method described hereinabove in the preparation of a pharmaceutical composition for use in the treatment of a disorder associated with accumulation of misfolded proteins as defined above.

The above methods may be used to screen for a ligand useful as an inhibitor of PPP1R15A-PP1.

Compounds of general formula (I) are useful both as laboratory tools and as therapeutic agents. In the laboratory certain compounds of the invention are useful in establishing whether a known or newly discovered target contributes a critical or at least significant biochemical function during the establishment or progression of a disease state, a process commonly referred to as 'target validation'.

The present invention is further described with reference to the following figures, wherein:

BRIEF DESCRIPTION OF THE DRAWINGS

FIG. 2 shows that translation is attenuated 2 h following Tunicamycin addition. Translation recovery is noticeable in cells treated with tunicamycin only. Example 1 of the invention prolongs translation attenuation in tunicamycin treated cells. See description test 3.

Figure 1:
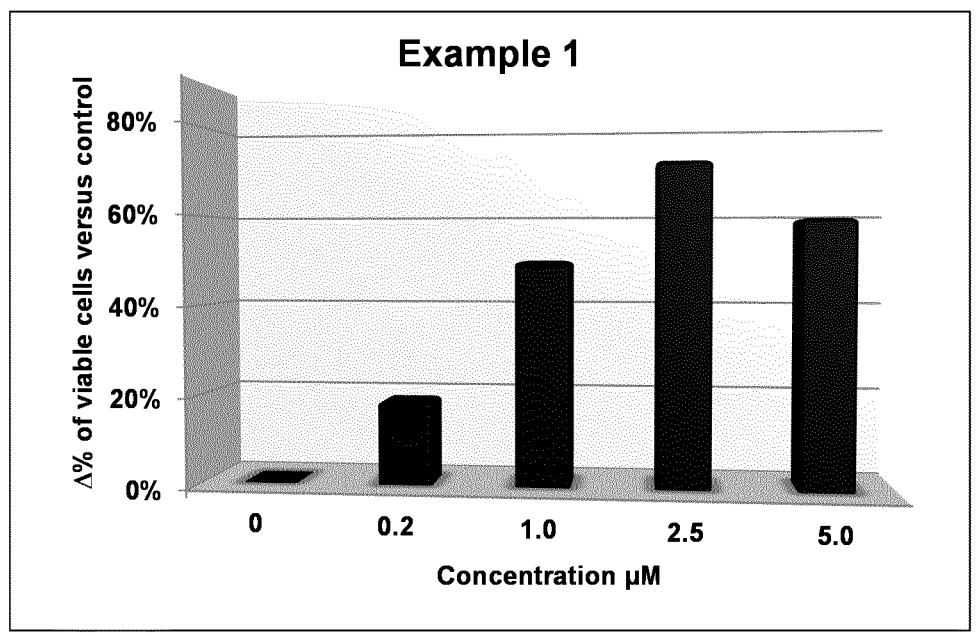
FIG. 1 shows dose dependent protection of HeLa cells by Compound of the formula (I), Example 1 of the invention, from ER stress induced by 6 hour exposure to tunicamycin. See description test 1.
Figure 2:
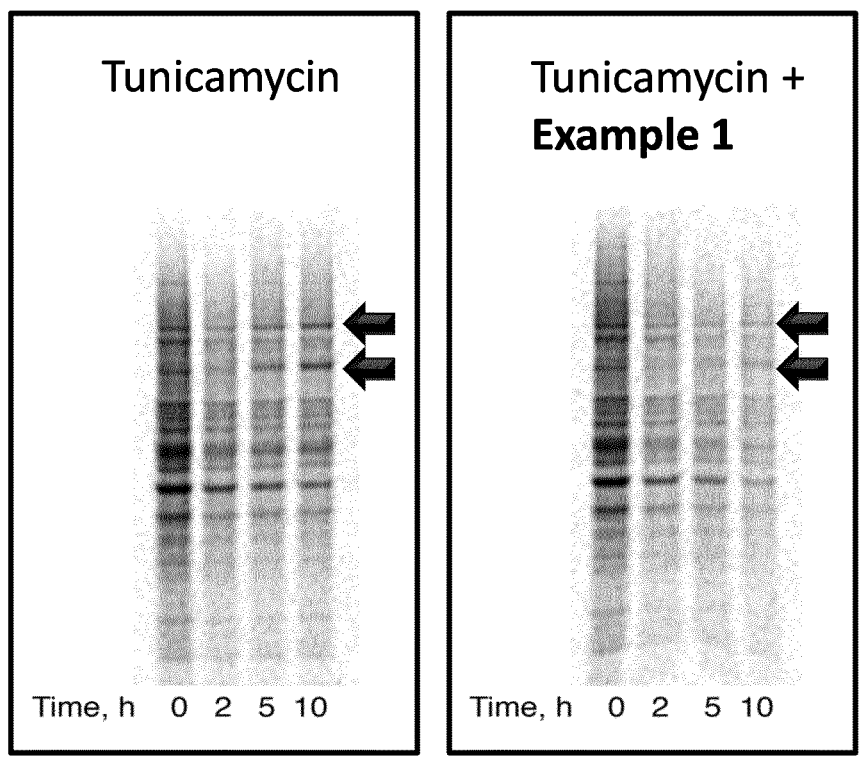
FIG. 2 shows that Compound of the formula (I), Example 1 of the invention, postpones translation recovery in stressed cells. More specifically.

The present invention is further described with reference to the following non-limiting examples.

EXAMPLES

Methods & Materials

Example 1 was purchased from Chemdiv ref: 1683-6588
Example 2 was purchased from Chembridge ref: 5173161
Example 4 was purchased from Enamine ref: Z49562642
Example 6 was purchased from Chemdiv ref: 1683-6502
Preparation of the Compounds According to the Present Invention The reactants and commercials compounds were purchased from Acros Organics, Sigma-Aldrich. The compounds according to the present invention can be prepared according to the following general procedure:
General Procedure A:

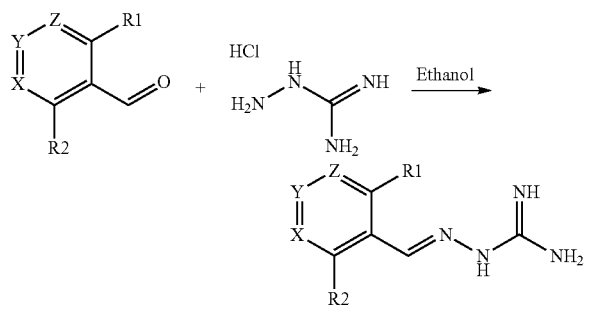

To a solution of benzaldehyde (1 eq.) in ethanol (300 ml) was sequentially added Aminoguanidine hydrochloride (1 eq.) and sodium acetate (1 eq.) at 25° C. The resulting reaction mixture was heated at 80° C. for next ~6 hours. Reaction completion was monitored on TLC using dichloromethane/methanol (8/2) as mobile phase. After completion of reaction, the reaction mixture was allowed to cool down to 25° C. and dumped in the saturated solution of NaHCO$_3$ (700 ml). The resulting precipitate were filtered off under vacuum and washed with water (100 ml). The resulting solid material was titurated with diethylether (2×25 ml) and dried under vacuum to provide the desired substituted aminoguanidine derivative.

The following compounds were prepared according general procedure A:

Example 1

1-[(E)[(2-chlorophenyl)methylidene]amino]-guanidine

Prepared following general procedure A from 2-chlorobenzaldehyde. $^1$H-NMR (DMSO-d$_6$): δ (ppm) 5.61 (s, 2H); 6.06 (s, 2H); 7.22-7.32 (m, 2H); 7.40 (dd, 1H); 8.15 (dd, 1H); 8.28 (s, 1H); MS (ESI+): m/z=197.4 [M+H]$^+$ Example 3

1-[(E)[(2-fluorophenyl)methylidene]amino]-guanidine

Prepared following general procedure A from 2-fluorobenzaldehyde.

Example 7

1-[(E)-[(2-chloro-4-fluorophenyl)methylidene]amino]guanidine

Prepared following general procedure A from 2-chloro-4-fluorobenzaldehyde in 67% yield. $^1$H-NMR (DMSO-d$_6$): δ (ppm) 5.80 (brs, 2H); 5.84 (brs, 2H); 7.19-7.34 (m, 4H); 8.16 (s, 1H); MS (ESI+): m/z=215.1 [M+H]$^+$ Example 13

1-[(E)-[(3-chloropyridin-4-yl)methylidene]amino]guanidine

Prepared following general procedure A from 3-chloroisonicotinaldehyde in 50% yield. $^1$H-NMR (DMSO-d$_6$): δ (ppm) 6.01 (brs, 2H); 6.33 (brs, 2H); 8.10 (d, 1H); 8.14 (s, 1H); 8.37 (dd, 1H); 8.52 (s, 1H); MS (ESI+): m/z=198.4 [M+H]$^+$ Example 15

1-[(E)-[(2-chloro-6-fluorophenyl)methylidene]amino]guanidine

Prepared following general procedure A from 2-chloronicotinaldehyde in 56% yield. $^1$H-NMR (DMSO-d$_6$): δ (ppm) 5.84 (brs, 2H); 5.88 (brs, 2H); 7.18-7.35 (m, 3H); 8.16 (s, 1H); MS (ESI+): m/z=215.4 [M+H]$^+$.

Intermediate 1: 3-chloro-5-fluoroisonicotinaldehyde

To a stirred solution of N,N-Diisopropylamine (0.864 g, 0.006690 mol) in THF (6 ml) was added n-buLi (1.6M in hexane) (7.6 ml, 0.012164 mol) dropwise over a period of 15 minutes at −78° C. The resulting reaction mixture was stirred at −78° C. for 15 minutes and then it was allowed to warm at 0° C. whereby it was further stirred for 1 hour. The resulting reaction mixture was again cooled at −78° C. and a solution of 3-chloro-5-fluoropyridine (0.8 g, 0.006082 mol) in THF (6 ml) was added dropwise over period of 10 minutes. The resulting reaction mixture was stirred at −78°

C. for 1 hour, thereafter methyl formate (0.73 g, 0.012164 mol) was added dropwise at −78° C. The resulting reaction mixture was further stirred at −78° C. for 1 more hour. The reaction was monitored on TLC using Hexane:ethylacetate (5:5) as mobile phase. After completion of reaction, the reaction mixture was dumped in saturated solution of $NH_4Cl$ (50 ml) and extracted with Ethyl acetate (4×25 ml). The combined organic extract was washed with demineralised water (50 ml), brine (25 ml), dried over sodium sulphate and concentrated under vacuo. Distillation of the organic layer provided the desired aldehyde (0.6 g, 61.85% yield) in crude form. This crude compound was directly used for the next step without any further treatment.

Example 16

1-[(E)-[(3-chloro-5-fluoropyridin-4-yl)methylidene]amino]guanidine

Prepared following general procedure A from 3-chloro-5-fluoroisonicotinaldehyde in 14% yield. $^1$H-NMR (DMSO-$d_6$): δ (ppm) 5.95-6.30 (m, 4H); 8.10 (s, 1H); 8.46-8.52 (m, 2H); MS (ESI+): m/z=216.0 $[M+H]^+$.

Example 8

N—{N-[(E)-[(2-chlorophenyl)methylidene]amino]carbamimidoyl}acetamide

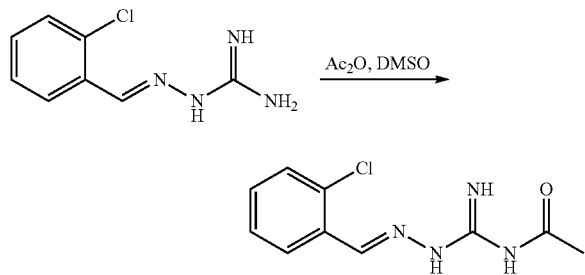

To a solution of 1-[(E)-[(2-chlorophenyl)methylidene]amino]-guanidine (0.50 g, 0.002543 mol) in DMSO (10 ml) was added acetic anhydride (0.26 g, 0.002543 mol) at 25° C. The resulting reaction mixture was stirred at 25° C. for next 15 hours. Reaction completion was monitored on TLC using dichloromethane/Methanol (9.5/0.5) as mobile phase. After completion of reaction the reaction mixture was dumped in the water (100 ml) and extracted with ethyl acetate (2×150 ml). The combined organic extract was washed with brine (100 ml), dried over sodium sulphate, filtered and concentrated in vacuo. The resulting crude material was further purified by flash chromatography using dichloromethane:methanol as mobile phase whereby the desired product eluted at around 1.0% methanol in dichloromethane. Distillation of the pure product fractions provided N—{N-[(E)-[(2-chlorophenyl)methylidene]amino]carbamimidoyl}acetamide (0.080 g, 13% yield). $^1$H-NMR (DMSO-$d_6$): δ (ppm) 2.97 (s, 3H); 7.25-7.41 (m, 3H); 7.42-7.53 (m, 1H); 7.79 (brs, 1H); 8.22-8.29 (m, 1H); 8.48 (s, 1H); 10.58 (brs, 1H); MS (ESI+): m/z=239.2 $[M+H]^+$.

Example 9 methyl N—{N-[(E)-[(2-chlorophenyl)methylidene]amino]carbamimidoyl}carbamate

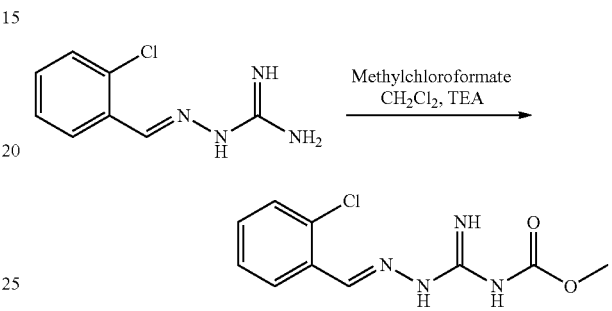

To a suspension of 1-[(E)-[(2-chlorophenyl)methylidene]amino]-guanidine (0.15 g, 0.000762 mol) in dichloromethane (5 ml) was added triethylamine (0.32 ml, 0.002288 mol) at 25° C. The resulting reaction mixture was cooled to 0° C. using ice/salt bath; thereafter methylchloroformate (0.09 ml, 0.001144 mol) was added in to the reaction mixture at 0° C. The resulting reaction mixture was stirred at room temperature for 15 hours. Reaction completion was monitored on TLC using dichloromethane/methanol (9/1) as mobile phase. After completion of reaction, the reaction mixture was dumped in saturated solution of $NaHCO_3$ (20 ml) and extracted with dichloromethane (3×25 ml). The combined organic extract was washed with D.M. water (20 ml), brine (20 ml), dried over sodium sulphate, filtered and concentrated in vacuo. The resulting crude material was further purified by flash column chromatography using dichloromethane:methanol as mobile phase whereby the desired product eluted at around 1.0% methanol in dichloromethane. Distillation of the pure product fractions provided methyl N—{N-[(E)-[(2-chlorophenyl)methylidene]amino]carbamimidoyl}carbamate (0.065 g, 37% yield). $^1$H-NMR (DMSO-$d_6$): δ (ppm) 3.60 (s, 3H); 7.34-7.43 (m, 2H); 7.45-7.52 (m, 1H); 7.67 (brs, 1H); 7.92 (brs, 1H); 8.22-8.30 (m, 1H); 8.44 (s, 1H); 11.02 (brs, 1H); MS (ESI+): m/z=255.4 $[M+H]^+$.

Selected compounds according to the invention are set forth in Table 1 below:

| Compound Number | Structure | Chemical Name |
| --- | --- | --- |
| Example 1 | 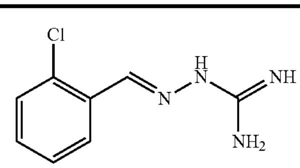 | 1-[(E)-[(2-chlorophenyl)methylidene]amino]-guanidine |

-continued

| Compound Number | Structure | Chemical Name |
| --- | --- | --- |
| Example 2 | 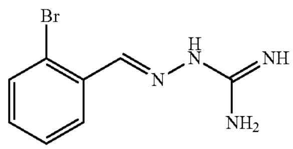 [SMILES: N=C(N)N/N=C/c1ccccc1Br] | 1-[(E)-[(2-bromophenyl)methylidene]amino]-guanidine |
| Example 3 | 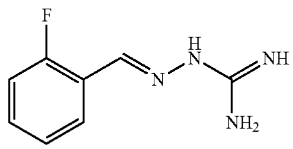 [SMILES: N=C(N)N/N=C/c1ccccc1F] | 1-[(E)-[(2-fluorophenyl)methylidene]amino]-guanidine |
| Example 4 | 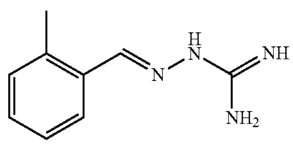 | 1-[(E)-[(2-methylphenyl)methylidene]amino]-guanidine |
| Example 6 | 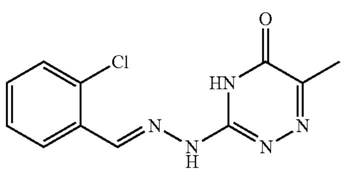 [SMILES: Cc1nnc(N/N=C/c2ccccc2Cl)[nH]c1=O] | 2-chlorobenzaldehyde (6-methyl-5-oxo-4,5-dihydro-1,2,4-triazin-3-yl)hydrazone |
| Example 7 | 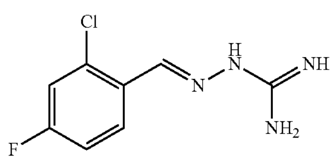 [SMILES: N=C(N)N/N=C/c1ccc(F)cc1Cl] | 1-[(E)-[(2-chloro-4-fluorophenyl)methylidene]amino]-guanidine |
| Example 8 | 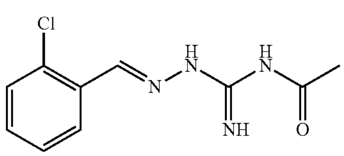 [SMILES: CC(=O)NC(=N)N/N=C/c1ccccc1Cl] | N-{N-[(E)-[(2-chlorophenyl)methylidene]amino]-carbamimidoyl}acetamide |
| Example 9 | 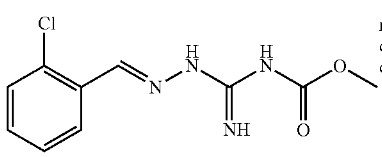 | methyl N-{N-[(E)-[(2-chlorophenyl)methylidene]amino]-carbamimidoyl}carbamate |
| Example 13 | 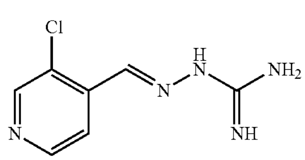 [SMILES: N=C(N)N/N=C/c1ccncc1Cl] | 1-[(E)-[(3-chloropyridin-4-yl)methylidene]amino]guanidine |

-continued

| Compound Number | Structure | Chemical Name |
|---|---|---|
| Example 15 | [structure] | 1-[(E)-[(2-chloro-6-fluorophenyl)methylidene]amino]-guanidine |
| Example 16 | [structure] | 1-[(E)-[(3-chloro-5-fluoropyridin-4-yl)methylidene]amino]guanidine |

In some of the experiments below, the salt of these compounds may be used; for example, the acetate salt of example 1 formed with acetic acid may be used.

Cytoprotection from ER Stress (Test 1)

HeLa cells were cultured in Dulbecco's Modified Eagle's Media (DMEM) supplemented with penicillin, streptomycin, containing 5% fetal bovine serum (FBS), at 37° C. in 5% $CO_2$ atmosphere. Cells were plated in 24 well plates at a density of 15,000 cells/ml 24 hours prior treatment. ER stress was elicited by addition of fresh media containing 2.5 µg/ml tunicamycin (Sigma-Aldrich) together with eIF2α phosphatases inhibitors (0.2-5 µM). Media were changed 6 h later with fresh media containing phosphatase inhibitors (0.2-5 µM). Inhibitors were dissolved in DMSO (50 mM) and DMSO was used as a mock treatment. Cell viability was assessed by measuring the reduction of WST-8 [2-(2-methoxy-4-nitrophenyl)-3-(4-nitrophenyl)-5-(2,4-disulfo-phenyl)-2H-tetrazolium] into formazan using Cell viability Counting Kit-8 (Dojindo) according to the supplier's recommendation, 48 h after tunicamycin treatment. Cytoprotection from ER stress is measured in terms of the percentage increase in viable cells (relative to control) after ER stress. The result for Example 1 of the invention is shown in FIG. 1.

Assessment of Translation Rates in Unstressed Cells (Test 2)

HeLa cells (80,000 cells/nil) were plated in 12-well plates 24 h before each experiment and either untreated or treated with compounds (50 µM) for 0.5, 1, 2.5, 5 and 7.5 h. At the end of each time point, 30.6 µCi/ml $^{35}$S-methionine (EasyTag, PerkinElmer) was added to the culture medium for 10 min at 37° C. Following labelling, cells were washed with ice-cold PBS and lysed in 75 µl Laemmli Buffer. Lysates were sonicated, boiled at 95° C. for 5 min and resolved on NuPAGE 4-12% gradient gels. Gels were then stained with Coomassie Brilliant Blue R-250 and analyzed by phosphorimaging.

Assessment of Translation Rates in Stressed Cells (Test 3)

Figure 3:
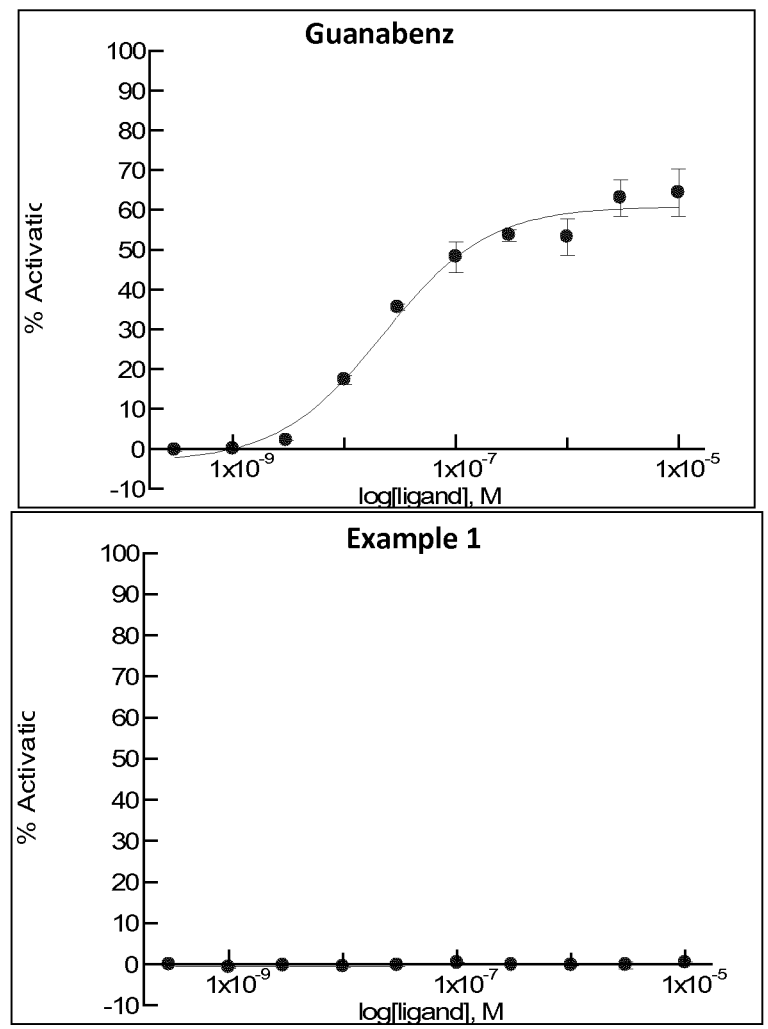
FIG. 3 shows Compound of the formula (I), Example 1 of the invention, unlike Guanabenz, has a no activity for adrenergic α2A receptor as measured by a functional assay for the adrenergic α2A receptor. See description test 5.

Treatments were performed as for measuring translation in unstressed cells, except that Tunicamycin (2.5 µg/ml) was added together with the compounds. The result for Example 1 of the invention is shown in FIG. 3.

Immunoprecipitations (Test 4)

HeLa cells (80,000 cells/nil) were plated the day before the indicated treatments, transfected with GFP-PPP1R15A or FLAG-PPP1R15B expression plasmids using Lipofectamine 2000 (Invitrogen) according to manufacturer's procedure. Two days following transfection, cells were treated for 6 h with compounds (50 µM) and then washed in PBS and lysed in IP buffer (50 mM Tris pH 7.4, 150 mM NaCl, 0.2% Triton X-100, 10% glycerol, and EDTA-free protease inhibitor cocktail). Lysates were clarified by centrifugation at 15,000 g for 15 min at 4° C. and pre-cleared on protein G beads for 1 hour at 4° C. Proteins were immunoprecipitated with 1.5 µl GFP antibody (JL-8, Clontech, 632380), bound to 20 µl of protein-G-sepharose beads (GE Healthcare, 17-0618-01). The beads were then washed 3 times with cold IP buffer and boiled in 50 µl Laemmli Buffer (25 mM Tris-HCl pH 6.8, 1% SDS, 25 mM DTT, 7.5% Glycerol, 0.05% Bromophenol blue). The immuno-precipitated protein complexes (17 µl) were separated on 4-12% NuPAGE gradient gels (Invitrogen), transferred to Optitran BA-S 83 reinforced Nitrocellulose membrane and revealed with GFP and PP1 antibodies (sc-7482, Santa Cruz).

Functional Aequorin Assay for Adrenergic α2A Receptor (Test 5)

CHO-K1 cells coexpressing mitochondrial apoaequorin, Gα16 and recombinant human Adrenergic α2A receptor grown to mid-log phase in culture media without antibiotics were detached with PBS-EDTA, centrifuged and resuspended in DMEM/HAM's F12 with HEPES, without phenol red+0.1% BSA protease free buffer at a concentration of $1 \times 10^6$ cells/ml. Cells were incubated at room temperature for at least 4 h with coelenterazine h. On each day of the test, reference agonist (UK14304) was tested to evaluate the performance of the assay and determine $EC_{50}$. Then, 50 µl of cell suspension was mixed with 50 µl of test agonist in a 96-well plate. The resulting emission of light was recorded using Hamamatsu Functional Drug Screening System 6000 luminometer. To standardize the emission of recorded light (determination of the "100% signal") across plate and across different experiments, some of the wells contained 100 µM digitonin or a saturating concentration of AT (20 µM).

Dose-response data from test compounds were analysed with XLfit (IDBS) software using nonlinear regression applied to a sigmoidal dose-response model.

Figure 4:
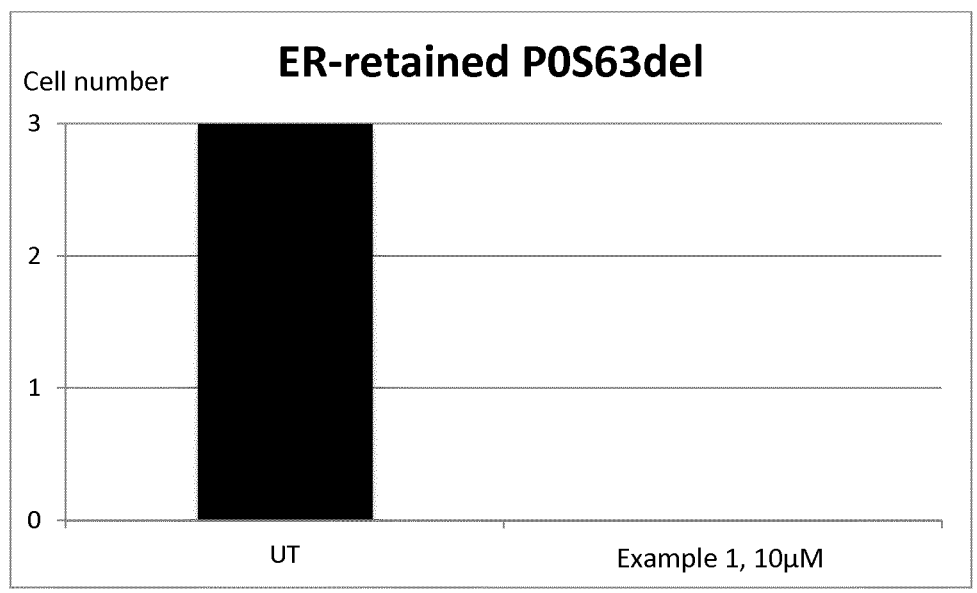
FIG. 4 shows that a Compound of the formula (I), Example 1 of the invention prevents ER-retention of P0S63del, the mutant protein associated with Charcot Marie Tooth 1B. Y axis: number of cells. UT: untreated.

The result for Example 1 of the invention is shown in FIG. 4. Advantageously, in contrast to Guanabenz, Example 1 is not considered to be a potent alpha-2 agonist. This loss in alpha-2 adrenergic activity renders the compound therapeutically useful in the treatment of the disorders claimed herein. The absence of alpha-2 adrenergic activity means that the compound can be administered at a dosage suitable to treat the disorders claimed herein, but without any significant effect on blood pressure, thereby avoiding the need to co-administer with a known alpha-2 adrenergic antagonist (an alpha blocker).

Selectivity Assessment

Selectivity was inferred from the results of test 1, 2, 3, and 5:

A selective inhibitor of PPP1R15A should, protect cells from ER stress (Test 1), does not inhibit translation in non-stressed cells (Test 2), prolongs translation attenuation after Tunicamycin (Test 3), and selectively dissociates PPP1R15A-PP1 holophosphatase but not PPP1R15b-PP1 holophosphatase (Test 4).

Results

The results of Tests 1 to 4 for selected compounds of the invention are shown below in Table 1.

TABLE 1

| Ex | Test 1 Survival following ER stress (increase %) | Test 2 Translation inhibition in non-stressed cells | Test 3 Translation attenuation after Tm | Test 4 Dissociation PPP1R15A/PP1 or PPP1R15B/PP1[b] | Selectivity assessment Selectivity towards PPP1R15A or PPP1R15B[a] |
|---|---|---|---|---|---|
| 1 | 180 | NO | prolonged | Dissociation PPP1R15A/PP1 BUT NOT PPP1R15B/PP1[b] | Selectively inhibits PPP1R15A, NOT PPP1R15B |
| 2 | 40 | YES | prolonged | | Inhibits both PPP1R15A and PPP1R15B |
| 3 | 80 | YES | prolonged | | Preferentially inhibits PPP1R15A |
| 4 | 100 | YES | prolonged | | Inhibits both PPP1R15A and PPP1R15B |
| 6 | 120 | NO | prolonged | | Selectively inhibit PPP1R15A, not B |
| 7 | 160 | YES | prolonged | Dissociation PPP1R15A/PP1 AND PPP1R15B/PP1[b] | Inhibits both PPP1R15A and PPP1R15B |
| 8 | 100 | YES | prolonged | | Inhibits both PPP1R15A and PPP1R15B |
| 9 | 20 | | | | |
| 13 | 60-80 | | | | |
| 15 | 160 | NO | prolonged | | Potentially selective |
| 16 | 140 | YES | | | Potentially non selective |

[a]inferred from translation inhibition in stressed/non-stressed cells
[b]confirms selectivity towards PPP1 R15A-PP1 or lack thereof.

Cell-Based Assays:
Material and Methods
Cell Culture and Reagents 293T cells were maintained in Dulbecco's modified Eagle's medium supplemented with 10% fetal bovine serum and transfected in 6- or 12-well plates by using the calcium phosphate method leading usually to 70% transfection efficiency. Routinely, 45,000 cells/ml were plated before transfection as described in (Rousseau et al. 2009). Myelin P0S63del-DSred construct was described in (Pennuto et al. 2008), the Huntingtin construct was described in (Rousseau et al. 2009), the SOD1A4V construct is described in (Munch et al. 2011) and the P23H construct is described in (Mendes and Cheetham 2008).

Fluorescence Microscopy

Transfected cells were fixed with 4% paraformaldehyde and labeled with indicated antibodies. Micrographs were taken at 100× magnification on a Leica TCS SP2AOBS confocal microscope or Leica DMRB Fluorescence microscope.

Immunoblotting

Routinely, 70% confluent cells from a well of a 12-well plate were lysed in 140 μl of boiling Laemmli buffer (25 mM Tris-HCl, pH 6.8, 1% SDS, 25 mM dithiothreitol, 7.5% glycerol, 0.05% bromphenol blue) for immunoblot analysis. 18 μl of protein extracts were loaded on 2-12% NuPAGE gels and transferred to Optitran BA-S 83 reinforced nitrocellulose membrane (Whatman and Schleicher & Schuell). Equal loading of protein extracts analyzed by immunoblot was controlled by Ponceau Red staining and vimentin (data not shown). Membranes were saturated in 5% dried skimmed milk in phosphate-buffered saline and probed with Htt 2b4 antibody or HA antibody to reveal HA-tagged SOD1. The appropriate secondary antibody coupled to peroxidase was revealed using the SuperSignal West Pico Chemiluminescent kit (Pierce). Chemiluminescent images were acquired using the Chemi-Smart 5000 (Vilber-Lourmat) allowing quantitative detection of chemilumi-nescence. Signals of interest were quantified using ImageJ.

Assay for Charcot Marie Tooth 1B (Test 6)

Deletion of serine 63 from P0 (P0S63del) causes Charcot-Marie-Tooth 1B neuropathy in humans and a similar demyelinating neuropathy in transgenic mice. The mutant protein misfolds and accumulates in the ER, induces the UPR and fails to be incorporated into myelin (D'Antonio et al., 2009, J Neurosci Res, 87, 3241-9). 293T cells were transfected with labeled P0S63 del—P0S63del-DSred—and analyzed by confocal microscopy, 48 h post-transfection in the presence or absence of compound of formula (I). In accordance with the methodology described in (Pennuto et al. 2008), cells with ER-retained P0S63del-DSred were scored. FIG. 4 shows that in untreated cells, P0S63del accumulates in the ER but Example 1 prevents this accumulation. Since accumulation of misfolded P0 causes CMT-1B and having shown that Example 1 reduces accumulation of the disease-causing protein, the compound of formula (I) should be useful to treat CMT-1B as well as other forms of CMT where the disease causing-protein is misfolded and retained in the ER.

Assay for Huntington's Disease and Amyotrophic Lateral Sclerosis (Test 7)

We tested for accumulation of mutant huntingtin amino-terminal fragment (Htt48Q) associated with Huntington's disease and SOD1 mutant (A4V), associated with amyotrophic lateral sclerosis.

Figure 5:
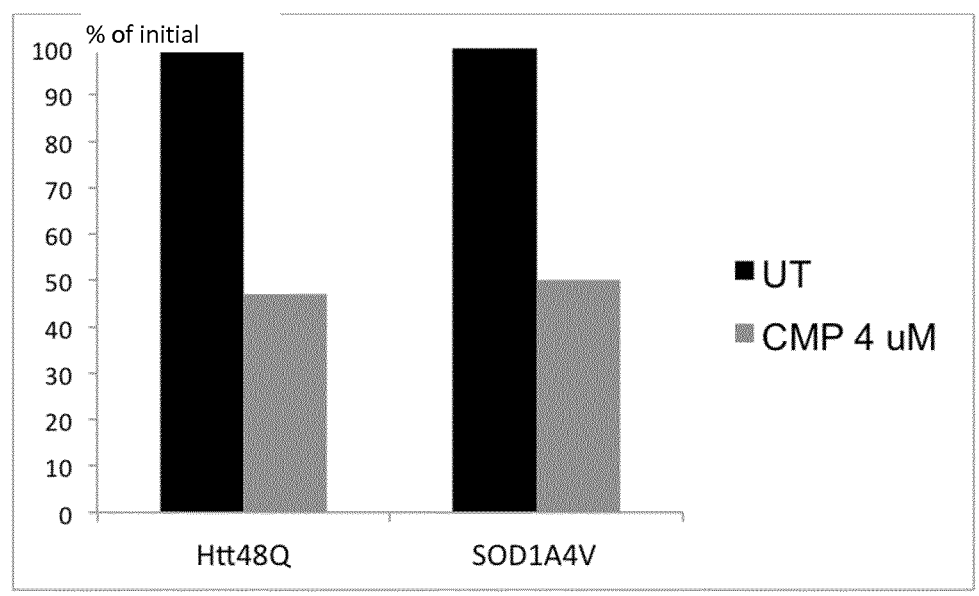
FIG. 5 shows that a Compound of the formula (I), Example 1 of the invention reduces accumulation of two unrelated disease-causing, misfolded proteins: mutant huntingtin amino-terminal fragment (Htt48Q) associated with Huntington's disease and SOD1 mutant (A4V), associated with amyotrophic lateral sclerosis. Y axis: percentage accumulation of protein, relative to untreated cells. UT: untreated.

We used a method previously described in WO/2008/041133. 293T cells were transfected with plasmids encoding for Htt48 or SOD1$^{A4V}$ and treated with Example 1 in DMSO or DMSO alone 4 h post-transfection. SDS lysates collected 48 h post-transfection were analyzed on a NuPAGE followed by immunoblot with Huntingtin antibody (2B4) or HA (SOD1). FIG. 5 shows the quantifications of the signal on immunoblots, normalized to untreated cells. Example 1 reduces accumulation of both proteins. Having shown that Example 1 reduces accumulation of the proteins causing Huntington's disease and Amyotrophic lateral sclerosis, the compound of formula (I) should be useful to treat such diseases as well as other neurodegenerative diseases caused by accumulation of misfolded proteins.

Assay for Rhodopsin P23H Aggregation (Test 8)

We tested for aggregation of rhodopsin associated for retinitis pigmentosa as described (Mendes & Cheetham 2008).

Figure 6:
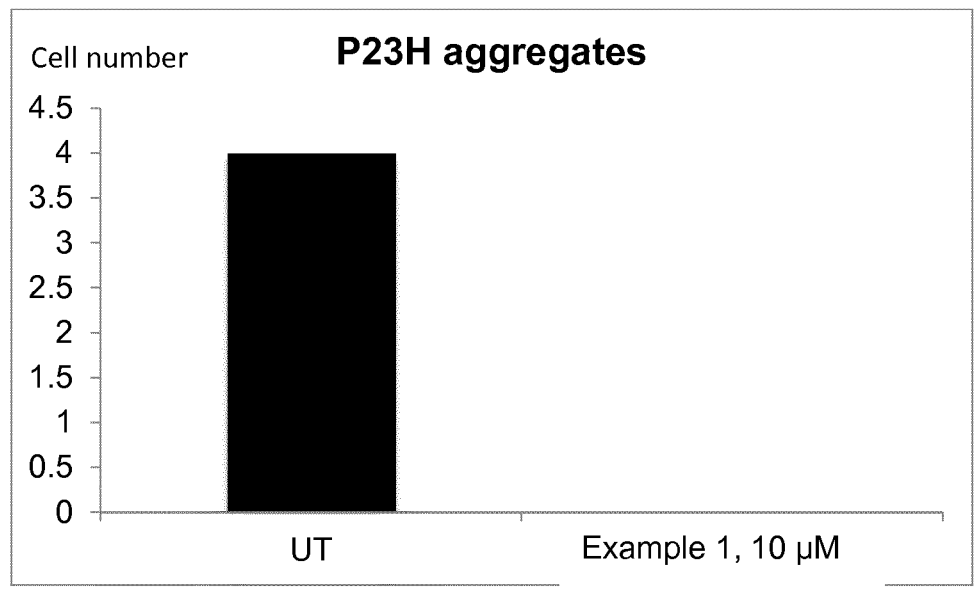
FIG. 6 shows that a Compound of the formula (I), Example 1 of the invention reduces accumulation of rhodopsin mutant P23H associated with retinitis pigmentosa. Y axis: number of cells. UT: untreated.

293T cells were transfected with plasmid encoding the P23H mutant of rhodopsin and treated with Example 1 in DMSO or DMSO alone 4 h post-transfection. Cells were analyzed by microscopy. FIG. 6 shows the cells with or without aggregates. Example 1 reduces aggregates. Since accumulation of misfolded rhodopsin causes RP and having shown that Example 1 reduces accumulation of the disease-causing protein, the compound of formula (I) should be useful to treat Retinitis Pigmentosa.

Examples 1 and 6 are confirmed selective inhibitors of PPP1R15A.

Examples 2, 4, 7, 8 inhibit both PPP1R15A and B.

Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

What is claimed is:

1. A method for treating Charcot Marie Tooth neuropathy or severe Dejerine-sottas syndrome in a subject in need thereof, the method comprising administering to the subject a therapeutically effective amount of a compound of formula (I), or a pharmaceutically acceptable salt thereof,

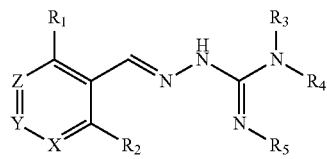

or a tautomer thereof,
wherein:
$R_1$ is alkyl, Cl, F or Br;
$R_2$ is H or F;
$R_3$ is selected from H and alkyl;
$R_4$ is selected from H and $C(O)R_6$;
$R_5$ is H;
$R_6$ is selected from $R_7$, $OR_7$ and $NR_8R_9$;
$R_7$, $R_8$ and $R_9$ are each independently selected from alkyl, cycloalkyl, aralkyl, cycloalkenyl, heterocyclyl and aryl, each of which is optionally substituted with one or more $R_{10}$ groups;
each $R_{10}$ is independently selected from halogen, OH, $NO_2$, CN, COO-alkyl, aralkyl, $SO_2$-alkyl, $SO_2$-aryl, COOH, CO-alkyl, CO-aryl, $NH_2$, NH-alkyl, $N(alkyl)_2$, $CF_3$, alkyl and alkoxy;
X and Z are each independently $CR_{11}$, and Y is selected from $CR_{11}$ and N;
$R_{11}$ is H or F.

2. The method according to claim 1 wherein $R_1$ is Cl, Br, Me, H or F.

3. The method according to claim 1 wherein $R_2$ is H.

4. The method according to claim 1 wherein Y is $CR_{11}$.

5. The method according to claim 1 wherein $R_3$ and $R_4$ are both H.

6. The method according to claim 1 wherein said compound is of formula (Ia), or a pharmaceutically acceptable salt thereof,

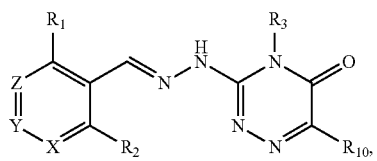

or tautomer thereof,
wherein $R_1$, $R_2$, $R_3$ and $R_{10}$ are as defined in claim 1.

7. The method according to claim 1 wherein the compound is

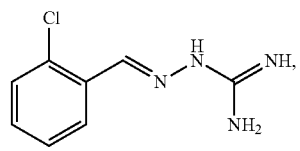
Example 1

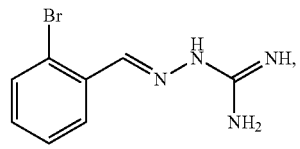
Example 2

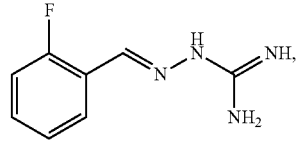
Example 3

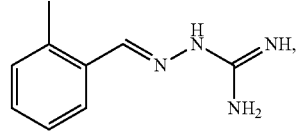
Example 4

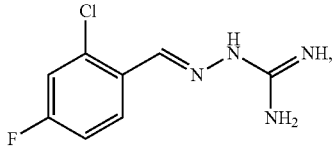
Example 7

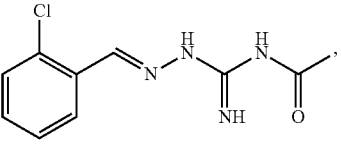
Example 8

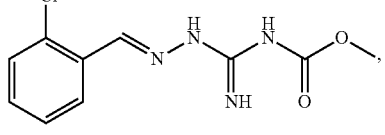
Example 9

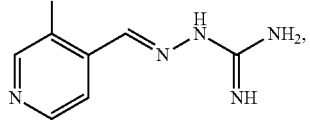
Example 13

-continued

Example 15

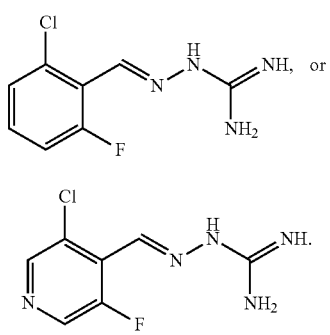

Example 16 or a tautomer thereof,
or a pharmaceutically acceptable salt of one of the foregoing.

8. The method according to claim 7 wherein the compound is

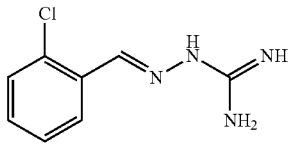

or a tautomer thereof,
or a pharmaceutically acceptable salt thereof.

9. A method of treating Charcot Marie Tooth neuropathy or severe Dejerine-sottas syndrome in a subject in need thereof, said method comprising administering to said subject a therapeutically effective amount of a compound of formula (II), or a pharmaceutically acceptable salt thereof,

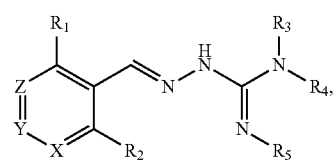

(II)

or a tautomer thereof
wherein:
$R_1$ alkyl, Cl, F or Br;
$R_2$ is H or F;
$R_3$ is selected from H and alkyl;
$R_4$ is selected from H and $C(O)R_6$;
$R_5$ is H;
$R_6$ is selected from $R_7$, $OR_7$ and $NR_8R_9$;
$R_7$, $R_8$ and $R_9$ are each independently selected from alkyl, cycloalkyl, aralkyl, cycloalkenyl, heterocyclic, aryl and heteroaryl, each of which is optionally substituted with one or more $R_{10}$ groups;
each $R_{10}$ is independently selected from halogen, OH, CN, $NO_2$, COO-alkyl, aralkyl, $SO_2$-alkyl, $SO_2$-aryl, COOH, CO-alkyl, CO-aryl, $NH_2$, NH-alkyl, $N(alkyl)_2$, $CF_3$, alkyl and alkoxy;
X and Z are each independently $CR_{11}$, and Y is N; and $R_{11}$ is H or F.

10. A method of treating Charcot Marie Tooth neuropathy or severe Dejerine-sottas syndrome in a subject in need thereof, said method comprising administering to said subject a therapeutically effective amount of a compound of formula (III), or a pharmaceutically acceptable salt thereof,

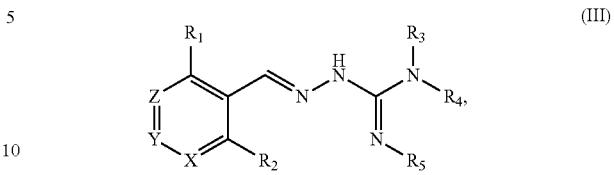

(III)

or a tautomer thereof,
wherein:
$R_1$ is alkyl, Cl, F or Br;
$R_2$ is H or F;
$R_3$ is selected from H and alkyl;
$R_4$ is $C(O)R_6$;
$R_5$ is H;
$R_6$ is selected from $R_7$, $OR_7$ and $NR_8R_9$;
$R_7$, $R_8$ and $R_9$ are each independently selected from alkyl, cycloalkyl, aralkyl, cycloalkenyl, heterocyclic, aryl and heteroaryl, each of which is optionally substituted with one or more $R_{10}$ groups;
each $R_{10}$ is independently selected from halogen, OH, CN, $NO_2$, COO-alkyl, aralkyl, $SO_2$-alkyl, $SO_2$-aryl, COOH, CO-alkyl, CO-aryl, $NH_2$, NH-alkyl, $N(alkyl)_2$, $CF_3$, alkyl and alkoxy;
X and Z are each independently $CR_{11}$, and Y is selected from $CR_{11}$ and N; and $R_{11}$ is H or F.

11. A method of treating Charcot Marie Tooth neuropathy or severe Dejerine-sottas syndrome in a subject in need thereof, said method comprising administering to said subject a therapeutically effective amount of a compound of formula (IV), or a pharmaceutically acceptable salt thereof,

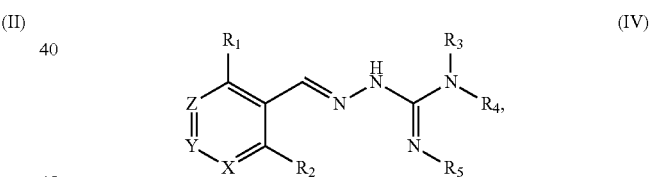

(IV)

or a tautomer thereof,
wherein:
$R_1$ is alkyl or Br;
$R_2$ is H;
$R_3$ is selected from H and alkyl;
$R_4$ is selected from H and $C(O)R_6$;
$R_5$ is H;
$R_7$, $R_8$ and $R_9$ are each independently selected from alkyl, cycloalkyl, aralkyl, cycloalkenyl, heterocyclyl and aryl, each of which is optionally substituted with one or more $R_{10}$ groups;
each $R_{10}$ is independently selected from halogen, OH, CN, $NO_2$, COO-alkyl, aralkyl, $SO_2$-alkyl, $SO_2$-aryl, COOH, CO-alkyl, CO-aryl, $NH_2$, NH-alkyl, $N(alkyl)_2$, $CF_3$, alkyl and alkoxy;
X and Z are each CH and Y is $CR_{11}$;
$R_{11}$ is H or F.

12. A method of treating Charcot Marie Tooth neuropathy or severe Dejerine-sottas syndrome in a subject in need thereof, said method comprising administering to said subject a therapeutically effective amount of a compound selected from the following, and pharmaceutically acceptable salts thereof,
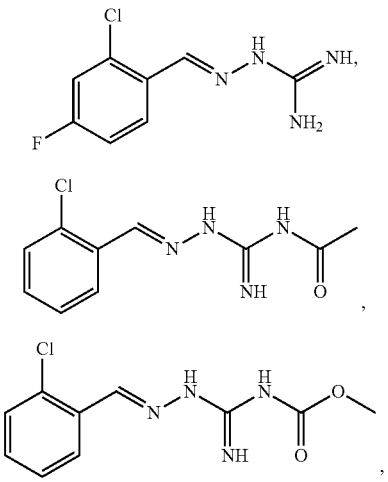
Example 7
Example 8
Example 9
-continued
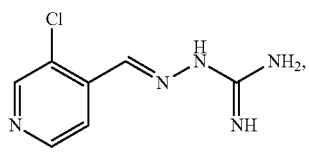
Example 13
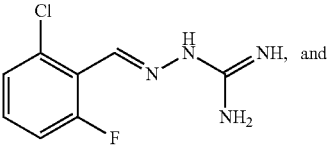
Example 15
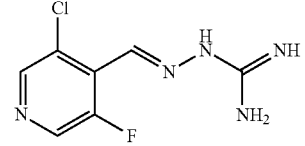 [SMILES: N=C(N)N/N=C/c1c(F)cncc1Cl]
Example 16
or a tautomer thereof.
13. The method according to claim 1 wherein $R_1$ is Cl.
* * * * *